US008788213B2

(12) United States Patent
Bright et al.

(10) Patent No.: US 8,788,213 B2
(45) Date of Patent: Jul. 22, 2014

(54) LASER MEDIATED SECTIONING AND TRANSFER OF CELL COLONIES

(75) Inventors: Gary Bright, San Diego, CA (US); Kristi Hohenstein, Carlsbad, CA (US); Anuradha Soundararajan, San Diego, CA (US); Manfred Koller, San Diego, CA (US)

(73) Assignee: Intrexon Corporation, Blacksburg, VA (US)

(*) Notice: Subject to any disclaimer, the term of this patent is extended or adjusted under 35 U.S.C. 154(b) by 435 days.

(21) Appl. No.: 12/686,359

(22) Filed: Jan. 12, 2010

(65) Prior Publication Data

US 2010/0184119 A1 Jul. 22, 2010

Related U.S. Application Data

(60) Provisional application No. 61/144,101, filed on Jan. 12, 2009.

(51) Int. Cl.
| G06F 19/00 | (2011.01) |
| G06F 19/10 | (2011.01) |
| G01N 1/28 | (2006.01) |
| G06K 9/00 | (2006.01) |
| G06K 9/20 | (2006.01) |

(52) U.S. Cl.
USPC ........... 702/19; 702/21; 435/40.5; 435/40.51; 382/128; 382/133; 382/282

(58) Field of Classification Search
None
See application file for complete search history.

(56) References Cited

U.S. PATENT DOCUMENTS

| 3,674,926 A | 7/1972 | Dewey et al. |
| 3,864,571 A | 2/1975 | Stillman et al. |
| 4,000,417 A | 12/1976 | Adkisson et al. |
| 4,165,149 A | 8/1979 | Suzki et al. |
| 4,284,897 A | 8/1981 | Sawamura et al. |
| 4,395,397 A | 7/1983 | Shapiro |
| 4,532,402 A | 7/1985 | Overbeck |
| 4,624,915 A | 11/1986 | Schindler et al. |
| 4,629,687 A | 12/1986 | Schindler et al. |
| 4,803,992 A | 2/1989 | Lemelson |
| 4,950,592 A | 8/1990 | Daiss |
| 4,998,284 A | 3/1991 | Bacus et al. |
| 5,013,660 A | 5/1991 | Kasuya et al. |
| 5,031,099 A | 7/1991 | Kettler |
| 5,035,693 A | 7/1991 | Kratzer et al. |
| 5,053,693 A | 10/1991 | Bohnert et al. |
| 5,072,382 A | 12/1991 | Kamentsky |
| 5,089,384 A | 2/1992 | Hale |
| 5,093,866 A | 3/1992 | Douglas-Hamilton et al. |
| 5,103,660 A | 4/1992 | Johnson |
| 5,109,276 A | 4/1992 | Nudelman et al. |
| 5,158,889 A | 10/1992 | Hirako et al. |
| 5,188,633 A | 2/1993 | Kratzer et al. |
| 5,202,230 A | 4/1993 | Kamentsky |
| 5,235,522 A | 8/1993 | Bacus |
| 5,257,182 A | 10/1993 | Luck et al. |
| 5,272,081 A | 12/1993 | Weinreb et al. |
| 5,287,272 A | 2/1994 | Rutenberg et al. |
| 5,296,963 A | 3/1994 | Murakami et al. |
| 5,298,963 A | 3/1994 | Moriya et al. |
| 5,381,224 A | 1/1995 | Dixon et al. |
| 5,422,720 A | 6/1995 | Berndt |
| 5,428,690 A | 6/1995 | Bacus et al. |
| 5,432,865 A | 7/1995 | Kasdan et al. |
| 5,445,934 A | 8/1995 | Fodor et al. |
| 5,523,543 A | 6/1996 | Hunter, Jr. et al. |
| 5,548,661 A | 8/1996 | Price et al. |
| 5,552,605 A | 9/1996 | Arata |
| 5,590,168 A | 12/1996 | Iketaki |
| 5,646,411 A | 7/1997 | Kain et al. |
| 5,672,880 A | 9/1997 | Kain |
| 5,690,846 A | 11/1997 | Okada et al. |
| 5,713,364 A | 2/1998 | DeBaryshe et al. |
| 5,719,391 A | 2/1998 | Kain |
| 5,732,150 A | 3/1998 | Zhou et al. |
| 5,784,162 A | 7/1998 | Cabib et al. |
| 5,785,703 A | 7/1998 | Goodman et al. |
| 5,790,710 A | 8/1998 | Price et al. |
| 5,795,755 A | 8/1998 | Lemelson |
| 5,828,776 A | 10/1998 | Lee et al. |
| 5,874,266 A | 2/1999 | Palsson |
| 5,878,746 A | 3/1999 | Lemelson et al. |

(Continued)

FOREIGN PATENT DOCUMENTS

| DE | 195 29 371 | 2/1997 |
| EP | 0 534 247 | 3/1993 |

(Continued)

OTHER PUBLICATIONS

Szaniszlo et al. (Cytometry Part A (2006) vol. 69A, pp. 641-651).*
Tanaka et al. (Journal of Translational Medicine (2006) vol. 4, pp. 1-16).*
"Automated Stem Cell Passage powered by LEAP Physical Passage of ES and iPS Cell Colonies." (2009) LEAP Stem Cell Pass. Appl. Note; 1-2.
Bauwens, C., et al. "Control of Human Embryonic Stem Cell Colony and Aggregate Size Heterogeneity Influences Differentiation Trajectories." (2008) Stem Cells; 26:2300-2310.
Burridge, P., et al. "Improved Human Embryonic Stem Cell Embryoid Body Homogeneity and Cardiomyocyte Differentiation from a Novel V-96 Plate Aggregation System Highlights Interline Variability." (2007) Stem Cells; 25:929-938.

(Continued)

Primary Examiner — Lori A Clow
(74) Attorney, Agent, or Firm — Knobbe, Martens, Olson & Bear LLP

(57) ABSTRACT

Disclosed herein are methods and devices for sectioning cell colonies. Also disclosed are methods of purifying cell colonies. A method of sectioning cell colonies can include providing a cell colony on a culture plate comprising a known thickness; positioning a bottom of the culture plate using automated focus technology; and sectioning the cell colony into one or more pieces using a pattern of laser cutting lines. Devices for performing the method are also disclosed.

23 Claims, 24 Drawing Sheets

(56) References Cited

U.S. PATENT DOCUMENTS

| | | |
|---|---|---|
| 5,890,846 A | 4/1999 | Clark et al. |
| 5,891,656 A | 4/1999 | Zarling et al. |
| 5,932,872 A | 8/1999 | Price |
| 5,952,651 A | 9/1999 | Morito et al. |
| 5,995,645 A | 11/1999 | Soenksen et al. |
| 6,005,256 A | 12/1999 | McGlynn et al. |
| 6,007,814 A | 12/1999 | Scheinberg |
| 6,040,139 A | 3/2000 | Bova |
| 6,099,522 A | 8/2000 | Knopp et al. |
| 6,122,396 A | 9/2000 | King et al. |
| 6,143,535 A | 11/2000 | Palsson |
| 6,148,096 A | 11/2000 | Pressman et al. |
| 6,156,576 A | 12/2000 | Allbritton et al. |
| 6,166,385 A | 12/2000 | Webb et al. |
| 6,215,892 B1 | 4/2001 | Douglass et al. |
| 6,218,132 B1 | 4/2001 | Spack et al. |
| 6,221,596 B1 | 4/2001 | Yemini et al. |
| 6,275,777 B1 | 8/2001 | Shimizu |
| 6,298,264 B1 | 10/2001 | Zhong et al. |
| 6,315,772 B1 | 11/2001 | Marchitto et al. |
| 6,326,489 B1 | 12/2001 | Church et al. |
| 6,381,224 B1 | 4/2002 | Lane et al. |
| 6,424,863 B1 | 7/2002 | Flock et al. |
| 6,509,166 B1 | 1/2003 | Edberg |
| 6,514,722 B2 | 2/2003 | Palsson et al. |
| 6,534,308 B1 | 3/2003 | Palsson et al. |
| 6,642,018 B1 | 11/2003 | Koller et al. |
| 6,753,161 B2 | 6/2004 | Koller et al. |
| 6,759,206 B1 | 7/2004 | Rubin et al. |
| 6,804,385 B2 | 10/2004 | Eisfeld |
| 7,092,557 B2 | 8/2006 | Eisfeld et al. |
| 7,129,070 B2 | 10/2006 | Palsson |
| 7,132,289 B2 | 11/2006 | Kobayashi et al. |
| 7,300,795 B2 | 11/2007 | Koller et al. |
| 7,378,236 B1 | 5/2008 | Brown et al. |
| 7,425,426 B2 | 9/2008 | Koller et al. |
| 7,505,618 B2 | 3/2009 | Palsson et al. |
| 7,622,274 B2 | 11/2009 | Koller et al. |
| 7,713,733 B2 | 5/2010 | Cliffel et al. |
| 2002/0076744 A1 | 6/2002 | Koller et al. |
| 2003/0148335 A1 | 8/2003 | Shen et al. |
| 2003/0180902 A1 | 9/2003 | Palsson et al. |
| 2004/0071332 A1 | 4/2004 | Bruce et al. |
| 2004/0072278 A1 | 4/2004 | Chou et al. |
| 2005/0095578 A1 | 5/2005 | Koller et al. |
| 2005/0118652 A1 | 6/2005 | Lee et al. |
| 2006/0141616 A1 | 6/2006 | Guu et al. |
| 2007/0134809 A1 | 6/2007 | Cho et al. |
| 2007/0269875 A1 | 11/2007 | Koller et al. |
| 2008/0014605 A1 | 1/2008 | Palsson et al. |
| 2008/0050794 A1 | 2/2008 | Koller et al. |
| 2008/0066322 A1 | 3/2008 | Shin |
| 2008/0160090 A1 | 7/2008 | Oraevsky et al. |
| 2008/0166793 A1 | 7/2008 | Beer et al. |
| 2009/0175529 A1 | 7/2009 | Palsson et al. |
| 2009/0191619 A1 | 7/2009 | Eisfeld et al. |
| 2010/0086984 A1 | 4/2010 | Koller et al. |
| 2010/0136683 A1 | 6/2010 | Koller et al. |
| 2010/0179310 A1 | 7/2010 | Kamme et al. |
| 2010/0184119 A1 | 7/2010 | Bright et al. |

FOREIGN PATENT DOCUMENTS

| | | |
|---|---|---|
| EP | 0 594 282 | 4/1994 |
| EP | 0 662 512 | 7/1995 |
| EP | 1 011 697 B1 | 12/2006 |
| EP | 1745130 | 1/2007 |
| JP | 59-042885 | 3/1984 |
| JP | 63-259465 | 4/1987 |
| JP | 02-124143 | 5/1990 |
| JP | 02-280079 | 11/1990 |
| JP | 03-172167 | 7/1991 |
| JP | 05-177128 | 7/1993 |
| JP | 52-010052 | 8/1993 |
| JP | 07-174977 | 7/1995 |
| JP | 08-160309 | 6/1996 |
| JP | 10-075946 | 3/1998 |
| JP | 10-502466 | 3/1998 |
| JP | 10-185911 | 7/1998 |
| JP | 2000-275541 | 10/2000 |
| JP | 2001-518295 A | 10/2001 |
| JP | 2002-511843 | 4/2002 |
| JP | 2003-076569 | 3/2003 |
| JP | 2003-259076 | 9/2003 |
| JP | 2007-514407 | 7/2007 |
| JP | 2007-529221 | 11/2007 |
| RU | 2054486 C1 | 2/1996 |
| WO | WO 89/01630 | 2/1989 |
| WO | WO 95/20054 | 7/1995 |
| WO | WO 96/01438 | 1/1996 |
| WO | WO 96/18205 | 6/1996 |
| WO | WO 97/11156 | 3/1997 |
| WO | WO 97/28439 A1 | 8/1997 |
| WO | WO 98/30384 | 7/1998 |
| WO | WO 98/35256 | 8/1998 |
| WO | WO 98/38490 | 9/1998 |
| WO | WO 98/42356 | 10/1998 |
| WO | WO 98/52016 | 11/1998 |
| WO | WO 98/54294 | 12/1998 |
| WO | WO 99/16875 A1 | 4/1999 |
| WO | WO 00/34434 | 6/2000 |
| WO | WO 00/70528 | 11/2000 |
| WO | WO 01/40454 | 6/2001 |
| WO | WO 01/66030 | 9/2001 |
| WO | WO 01/68110 | 9/2001 |
| WO | WO 03/027224 | 4/2003 |
| WO | WO 03/099996 A2 | 12/2003 |
| WO | WO 2004/016212 A2 | 2/2004 |
| WO | WO 2007/147079 | 12/2007 |

OTHER PUBLICATIONS

Buzzard, J.J., et al. "Karyotype of human ES cells during extended culture." (2004) Nat. Biotechnol.; 22:381-382.
Draper, J.S., et al. "Recurrent gain of chromosomes 17q and 12 in cultured human embryonic stem cells." (2004) Nat. Biotechnol.; 22:53-54.
Hirvonen, J., et al. "Microcutting of Living Tissue Slices and Stem Cell Colonies by Using Mechanical Tool and Liquid Jet." (2008) Biomedical Robotics and Biomechatronics; 612-617.
Joannides, A., et al. "Automated Mechanical Passage: A Novel and Efficient Method for Human Embryonic Stem Cell Expansion." (2006) Stem Cells 24:230-235.
Mitalipova, M., et al. "Preserving the genetic integrity of human embryonic stem cells." (2005) Nat. Biotechnol; 23:19-20.
Murray, G.I., "An overview of laser microdissection technologies." (2007) 171-176.
Oh, S.K., et al. "Methods for Expansion of Human Embryonic Stem Cells." (2005) Stem Cells; 23:605-609.
Reubinoff, B.E., et al. "Embryonic stem cell lines from human blastocyst: somatic differentiation in vitro." (2000) Nat. Biotechnol; 18:399-404.
Stich, M., et al. "Live Cell Catapulting and Recultivation." (2003) Pathol. Res. Pract. 199: 405-409.
Takahashi, K., et al. "Induction of Pluripotent Stem Cells from Adult Human Fibroblasts by Defined Factors." (2007) Cell; 131: 861-872.
Terstegge, S., et al. "Automated maintenance of embryonic stem cell cultures." (2007) Biotechnol. Bioeng.; 96:195-201.
Thomson, H., "Bioprocessing of embryonic stem cells for drug discovery." Review. (2007) Trends Biotechnol.; 25:224-230.
Thomson J.A, et al. "Embryonic stem cell lines derived from human blastocysts." (1998) Science; 282:1145-1147.
Ungrin, M., et al. "Reproducible, ultra high-thoroughput formation of multicellular organization from single cell suspension-derived human embryonic stem cell aggregates." (2008) PLOS One; 3:1565-1-12.
Valamehr, B., et al. "Hydrophobic surfaces for enhanced differentiation of embryonic stem cell-derived embryoid bodies." (2008) PNAS; 105:14459-14464.

(56) References Cited

OTHER PUBLICATIONS

International Search Report and Written Opinion issued on the corresponding PCT Application No. PCT/US2010/020816, dated Jun. 4, 2010.
Andrews, P.W. et al. "Karyotype of human ES cells during extended culture." (2004) Nat. Biotechnol.; 22(4):381-382.
International Preliminary Examination Report dated Jul. 21, 2011 from International Application No. PCT/US2010/020562.
International Preliminary Examination Report dated Jul. 21, 2011 from International Application No. PCT/US2010/020816.
Extended European Search Report dated Aug. 1, 2011 from European Application No. EP 11001625.0.
Applicant's Response to Office Action dated May 3, 2011 in U.S. Appl. No. 11/711,426.
Office Action dated Jul. 15, 2011 in U.S. Appl. No. 11/711,426.
Office Action dated Aug. 2, 2011 in U.S. Appl. No. 12/972,305.
Office Action dated Oct. 27, 2011 in U.S. Appl. No. 13/030,082.
Decision to Grant dated Jul. 21, 2011 in European Application No. EP 00982344.4.
Grant dated Aug. 17, 2011 in European Application No. EP 00982344.4.
Applicant's Response to Written Opinion dated Aug. 4, 2011 in European Application No. 10175331.7.
Communication of Office Action dated Jul. 12, 2011 in Japanese Application No. JP 2001-542522.
Communication dated Jan. 26, 2011 in Canadian Application No. CA 2281112.
Applicant's Response to Communication dated Jul. 26, 2011 in Canadian Application No. CA 2281112.
Communication dated Sep. 6, 2011 in CA patent application No. CA 2281112.
Grant dated Jun. 9, 2011 in Japanese Application No. JP 2007-503988.
Communication dated Sep. 12, 2011 in European Application No. EP 11001625.0.
Aylward, Redmond P., "The Advances & Technologies of Galvanometer-based Optical Scanners," *Part of the SPIE Conference on Optical Scanning: Design and Application*, Denver, CO, Jul. 1999, SPIE vol. 3787, pp. 158-164.
Cohen et al., "MicroMaterials Processing," *Proceedings of the IEEE*, vol. 70, No. 6, Jun. 1982.
Corle, Timothy R., "Submicron Metrology in the Semiconductor Industry," *Solid-State Electronics* vol. 35, No. 3, pp. 391-402 (1992).
Corle et al., "Applications," *Confocal Scanning Optical Microscopy and Related Imaging Systems*, Copyright © 1996 by Academic Press, Chapter 5, pp. 277-322.
Flanagan et al., "Applications of High-Power Lasers in Electronic Assembly," *Key Engineering Materials* vols. 118-119, pp. 147-156 (1996).
Miller, Diane MSc., Monoclonal Antibody Production, *Stem Cell Technologies* (www.stemcell.com), Mini-Review, Cat. 29011, Ver. 1.0.0, pp. 1-2, downloaded from the web May 29, 2007.
O'Neill et al., "Germline transcription and expression of Tcrb-V8 genes in peripheral mouse lymphoid tissues," *Immunogenetics* (1995) 42: 309-314.
Wachter, Joseph R., "Laser-Based Semiconductor Fabrication," *Laser-Induced Plasmas and Applications*, Copyright © 1989 Marcel Dekker Inc., Chapter 6, pp. 269-294.
Office Action dated Nov. 1, 2011 in U.S. Appl. No. 12/986,792.
Applicant's Response to Office Action dated Mar. 1, 2012 in U.S. Appl. No. 12/986,792.
Notice of Allowance dated Jun. 5, 2012 in U.S. Appl. No. 12/986,792.
Applicant's RCE dated Sep. 5, 2012 in U.S. Appl. No. 12/986,792.
Applicant's Response to Office Action dated Feb. 1, 2012 in U.S. Appl. No. 12/972,305.
Office Action dated Mar. 1, 2012 in U.S. Appl. No. 12/972,305.
Restriction Requirement dated Dec. 19, 2011 in U.S. Appl. No. 12/684,854.
Applicant's Response to Restriction dated Jan. 17, 2012 in U.S. Appl. No. 12/684,854.
Office Action dated Mar. 22, 2012 in U.S. Appl. No. 12/684,854.
Applicant's Response to Office Action dated Jan. 27, 2012 in U.S. Appl. No. 13/030,082.
Notice of Allowance dated Mar. 16, 2012 in U.S. Appl. No. 13/030,082.
Supplemental Notice of Allowance dated Jun. 12, 2012 in U.S. Appl. No. 13/030,082.
Notice of Grant dated Aug. 28, 2012 in JP patent application No. 2001-542522.
Applicant's Response to Communication dated Mar. 6, 2012 in CA 2281112.
Examiner's Report dated Nov. 9, 2011 in CA 2,559,736.
Communication of JP Office Action dated Mar. 6, 2012 in JP patent application No. 2002-540540.
Applicant's Response to Communication of JP Office Action dated Jun. 6, 2012 in JP patent application No. 2002-540540.
Communication of Rejection of Appeal dated Aug. 23, 2012 in JP patent application No. 2002-540540.
Communication of Official Action dated Jan. 28, 2011 in JP Patent Application No. 2008-237226.
Applicant's Response to Official Action dated Jul. 28, 2011 in JP Patent Application No. 2008-237226.
Communication of Final Rejection dated Feb. 23, 2012 in JP Patent Application No. 2008-237226.
Applicant's Response of Notice of Appeal and Amendment to Communication dated Jun. 22, 2012 in JP Patent Application No. 2008-237226.
Communication dated Jul. 2, 2012 in JP Patent Application No. 2008-237226.
Applicant's Response to Communication dated Jul. 17, 2012 in JP Patent Application No. 2008-237226.
Japanese Office Action dated Jul. 2, 2013 for Japanese Patent Application No. JP 2011-033872, filed Feb. 18, 2011, which is related to captioned U.S. Appl. No. 12/686,359.
Office Action dated Dec. 13, 2012 in U.S. Appl. No. 12/684,854, filed Jan. 8, 2010.
Notice of Allowance dated Dec. 3, 2012 in U.S. Appl. No. 12/986,792, filed Jan. 7, 2011.
Allard et al., "Tumor Cells Circulate in the Peripheral Blood of All Major Carcinomas but not in Healthy Subjects or Patients with Non-malignant Diseases." Clin Cancer Res. (2004) 10(20):6897-904.
Almoguera et al., "Most Human Carcinomas of the Exocrine Pancreas Contain Mutant c-K-*ras* Genes." Cell (1988) 53: 549-554.
Andersen et al., "Failure of immunologic purging in mantle cell lymphoma assessed by polymerase chain reaction detection in minimal residual disease," Blood, 90: 4212-4221 (1997).
Atochina et al., "Comparison of results using the gel microdrop cytokine secretion assay with ELISPOT and intracellular cytokine staining assay," Cytokine 27 (2004) 120-128.
Bird et al., "4-Hydroperoxychyclophosphamide Purged Autologous Bone Marrow Transplantation in Non-Hodgkin's Lymphoma Patients at High Risk of Bone Marrow Involvement," Bone Marr. Transplan., 18:309-313 (1996).
Borth et al., "Efficient Selection of High-Producing Subclones During Gene Amplification of Recombinant Chinese Hamster Ovary Cells by Flow Cytometry and Cell Sorting," *Institute for Applied Microbiology* pp. 266-273 (2001).
Bos et al., "Prevalence of *ras* gene mutations in human colorectal cancers." Nature (1987) 327: 293-297.
Brezinsky et al. "A Simple Method for Enriching Populations of Transfected CHO Cells for Cells of Higher Specific Productivity", *Journal of Immunological Methods* 277 (2003) 141-155.
Brittberg et al., "Treatment of deep cartilage defects in the knee with autologous chondrocyte transplantation," N.E.J.Med., 331: 889-895 (1994).
Brockstein et al., "Tumor cell contamination of bone marrow harvest products: Clinical consequences in a cohort of advanced-stage breast cancer patients undergoing high-dose chemotherapy," J. Hematotherapy, 5: 617-624 (1996).
Brugger et al., "Mobilization of Tumor Cells and Hematopoietic Progenitor Cells Into Peripheral Blood of Patients with Solid Tumors," *Blood*, 83: 636-640 (1994).

(56) References Cited

OTHER PUBLICATIONS

Campana et al., "Detection of Minimal Residual Disease in Acute Leukemia: Methodological Advances and Clinical Significance," *Blood.*, 85: 1416-1434 (1995).

Cherlet et al., "Surface IgG Content of Murine Hybridomas: Direct Evidence for Variation of Antibody Secretion Rates During the Cell Cycle," *Biotechnology and Bioengineering*, vol. 47, pp. 535-540 (1995).

Chute et al., "Analysis of the steady-state dynamics organelle motion in cultured neurities," *Clin Exp Pharmco Physiol*, 22: 360 (1995).

Civin et al., "Cell Surface Antigens on Human Marrow Cells: Dissection of Hematopoietic Development Using Monoclonal Antibodies and Multiparameter Flow Cytometry," *International Journal of Cell Cloning* 5: 267-288 (1987).

Clarke et al., "A recombinant $bcl-x_s$ adenovirus selectively induces apoptosis in cancer cells but not in normal bone marrow cells," *Proc. Natl. Acad. Sci. USA*, 92: 11024-11028 (1995).

Cossman et al., "Reed-Sternberg cell genome expression supports a B-cell lineage," *Blood*, 94: 411-416 (1999).

Cyntellect, "Automated Stem Cell Passage Powered by Leap Physical Passage of ES and iPS Cell Colonies", LEAP™ Application Note, LAN008 Rev. 1.01/09, pp. 1-2 (2009).

Deisseroth et al., "Genetic marking shows that Ph$^+$ cells present in autologous transplants of chronic myelogenous leukemia (CML) contribute to relapse after autologous bone marrow in CML," *Blood*,83: 3068-3076 (1994).

Denk, Two-Photon Scanning Photochemical Microscopy: Mapping Ligand-Gated Ion Channel Distributions, Proc. Natl. Acad. Sci. 91:6629-6633 (1994).

Dixon et al., "Gene-expression analysis at the single-cell level." Trends in Pharmacological Sciences (2000) 21: 65-70.

Dooley et al., "A Novel, Inexpensive Technique for the Removal of Breast Cancer Cells from Mobilized Peripheral Blood Stem Cell Products," *Blood*, 88: 252a, Abstract 995, 438-11 (1996).

Edwards et al., "Flow Cytometric Separation of Gonadotrophs from Dispersed Rat Pituitaries Using a Fluorescent GnRH Antagonist," *Molecular and Cellular Endocrinology*, 30: 21-35(1983).

Elbashir et al., "Duplexes of 21-nucleotide RNAs mediate RNA interference in cultured mammalian cells." Nature, 411: 494-498 (2001).

El-Sayed et al., "Selective laser photo-thermal therapy of epithelial carcinoma using anti-EGFR antibody conjugated gold nanoparticles." Cancer Letters (2006) 239: 129-135.

Fields et al., "Clinical significance of bone marrow metastases as detected using the polymerase chain reaction in patients with breast cancer undergoing high-dose chemotherapy and autologous bone marrow transplantation," *J. Clin. Oncol.*, 14: 1868-1876 (1996).

Gazitt et al., "Purified CD34$^+$Lin$^-$Thy$^+$ Stem Cells Do Not Contain Clonal Myeloma Cells," *Blood*, 86: 381-389 (1995).

Gee, Adrian P., "Part 5: Autologous Bone Marrow Purging," *Bone Marrow Processing and Purging*, 248-328 (1991).

Goldman et al. "Motility of vinculin-deficient F9 embryonic carcinoma cells analyzed by video, laser confocal, and reflection interference contrast microscopy," *Experimental Cell Research* 221(2):311-319 (1995).

Grate et al., Laser-mediated, site-specific inactivation of RNA transcripts, *PNAS*, 96: 6131-6136 (1999).

Gray et al. "Secretion capture and report web: use of affinity derivatized agarose microdroplets for the selection of hybridoma cells" *Journal of Immunological Methods* 182 (1995) 155-163.

Greer et al., "A Clonogenic Culture Method for the Identification of Breast Cancer Cells in Marrow Aspirates of Patients Receiving High-Dose Chemotherapy," *Blood*, 88: 252a, Abstract 996, 439-II (1996).

Gribben et al., "Immunologic purging of marrow assessed by PCR before autologous bone marrow transplantation for B-cell lymphoma," *N.E.J. Med.*, 325: 1525-1533 (1991).

Gribben et al., "Antibody-mediated Purging; Bone Marrow Transplantation," *Boston-Blackwell Scientific Publications*, 149-163 (1994).

Gulati et al., "Rationale for Purging in Autologous Stem Cell Transplantation," *Journal of Hematotherapy*, 2: 467-471 (1993).

Gulliya et al "Elimination of Clonogenic Tumor Cells from HL-60, Daudi, and U-937 Cell Lines by Laser Photoradiation Therapy: Implications for Autologous Bone Marrow Purging" Blood 73(4):1059-1065 (1998).

Guo et al., "Laser-mediated gene transfer in rice," *Physiologia Plantarum*, 93: 19-24 (1995).

Han, et al. "Quantum-dot-tagged microbeads for multiplexed optical coding of biomolecules." Nat.Biotech., 19: 631-635 ( 2001).

Hanania et al., "A Novel Automated Method of Scanning Cytometry and Laser-Induced Necrosis applied to Tumor Cell Purging," Abstract #2836, Blood, Journal of the American Society of Hematology, Forty-First Annual Meeting, 3pages (Dec. 3-7, 1999).

Hanania et al., "Automated in Situ Measurement of Cell-Specific Antibody Secretion and Laser-Mediated Purification for Rapid Cloning of Highly-Secreting Producers." Biotechnol Bioeng. (2005) 30;91(7):872-6.

Holmes et al., "Improved cell line development by a high throughput affinity capture surface display technique to select for high secretors," Journal of Immunological Methods 230 (1999) 141-147.

Huang et al., "Symmetry of initial cell divisions among primitive hematopoietic progenitors is independent of ontogenic age and regulatory molecules," *Blood*, 94: 2595-2604 (1999).

Huang et al., "Plasmonic photothermal therapy (PPTT) using gold nanoparticles." Lasers in Medical Science. (2008) 23: 217-228.

Jasuja et al., "Chemotactic responses of *Escherichia coli* to small jumps of photoreleased L-aspartate," *Biophysical Journal*, 76: 1706-1719 (1999).

Jay, D. G., "Selective destruction of protein function by chromophore-assisted laser inactivation," *PNAS*, 85: 5454-5458 (1988).

Kah et al., "Combinatorial treatment of phototherapy using gold nanoshells with conventional photodynamic therapy to improve treatment efficacy: An in vitro study." Lasers in Surgery and Medicine. (2008) 40: 584-89.

Koller, M.R., "High-Throughput Laser-Mediated In Situ Cell Purification With High Purity and Yield." (2004) Cytometry; 61A: 153-161.

Krasieva, et al. "Cell Permeabilization and molecular transport by laser microirradiation." Proc.SPIE, 3260: 38-44 (1998).

Kurata, et al. "The laser method for efficient introduction of foreign DNA into cultured cells." Exp.Cell Res., 162: 372-378 (1986).

Langer et al., "The challenges ahead," *Sci. Am.*, 280: 86-89 (1999).

Lazarus et al., "Does In Vitro Bone Marrow Purging Improve the Outcome after Autologous Bone Marrow Transplantation?," *Journal of Hematotherapy*, 2: 457-466 (1993).

Letfullin et al.,"Laser-induced explosion of gold nanoparticles: potential role for nanophotothermolysis of cancer." Nanomed. (2006) 1(4):473-80.

Luo et al., "Gene expression profiles of laser-captured adjacent neuronal subtypes." Nat Med. (1999) 5(1):117-22.

Lydaki et al., "Merocyanine 540 mediated photoirradiation of leukemic cells. In vitro inference on cell survival," *Journal of Photochemistry and Photobiology B: Biology*, 32: 27-32 (1996).

Lydaki et al., "Merocyanine 540 mediated photolysis of normal bone marrow, committed hemopoietic progenitors and neoplastic cells. Implications for bone marrow purging," *Leukemia Research*, 21: 641-650 (1997).

Manz et al., "Analysis and sorting of live cells according to secreted molecules, relocated to a cell-surface affinity matrix," Proc. Natl. Acad. Sci. vol. 92, pp. 1921-1925 (Mar. 1995).

Mapara et al., "Monitoring of tumor cell purging after highly efficient immunomagnetic selection of CD34 cells from leukapheresis products in breast cancer patients: Comparison of immunocytochemical tumor cell staining and reverse transcriptase-polymerase chain reaction," *Blood*, 89: 337-344 (1997).

Mapara et al., "Combined Positive/Negative Purging and Transplantation of Peripheral Blood Progenitor Cell Autografts in Breast Patients: A Pilot Study," Exper. Hemat., 27:169-175 (1999).

Mashanov et al., "Visualizing Single Molecules Inside Living Cells Using Total Internal Reflection Fluorescence Microscopy," *Methods*; 29 (2003) 142-152.

(56) References Cited

OTHER PUBLICATIONS

McCoy et al., "Characterization of a human colon/lung carcinoma oncogene." Nature. (1983) 302(5903):79-81.
Meilhoc et al., "Application of Flow Cytometric Measurement of Surface IgG in Kinetic Analysis of Monoclonal Antibody Synthesis and Secretion by Murine Hybridoma Cells", *Journal of Immunological Methods*, 121 (1989) 167-174.
Merriam-Webster, Online Dictionary definition of "image". From www.m-w.com, accessed Sep. 14, 2005. 2 pages.
Miller et al., "Rapid Killing of Single Neurons by Irradiation of Intracellular Injected Dye," *Science*, 206: 702-704 (1979).
Miller, Diane MSc., Monoclonal Antibody Production, *Stem Cell Technologies* (www.stemcell.com), Cat. 29011, Mini-Review Ver. 1.0.0, pp. 1-2, retrieved from internet on May 29, 2007.
Nagrath et al., "Isolation of rare circulating tumour cells in cancer patients by microchip technology." Nature. (2007) 450(7173):1235-9.
Niemz, M. H., "Laser-tissue interactions: Fundamentals and applications," Springer-Verlag, (1996).
Nilius, et al. "A novel type of cardiac calcium channel in ventricular cells." Nature, 316: 443-6 (1985).
O'Brien et al., "Use of a multiparametric panel to target subpopulations in a heterogeneous solid tumor model for improved analytical accuracy," *Cytometry*, 21: 76-83 (1995).
Oh et al., "Phototoxicity of the Fluorescent Membrane Dyes PKH2 and PKH26 on the Human Hematopoietic KG1a Progenitor Cell Line," *Cytometry*, 36: 312-318 (1999).
Oleinick et al., "The Photobiology of photodynamic therapy: Cellular targets and mechanisms," *Rad. Res.*, 150: S146-S156 (1998).
Palumbo et al., "Targeted gene transfer in eukaryotic cells by dye-assisted laser optoporation," *J. Photochem. Photobiol.*, 36: 41-46 (1996).
Pastinen et al., "A System for Specific, High-throughput Genotyping by Allele-specific Primer Extension on Microarrays." Genome Res. (2000) 10(7):1031-42.
Paulus et al., "Purging peripheral blood progenitor cell grafts from lymphoma cells: Quantitative comparison of immunomagnetic $CD34^+$ selection systems," *Stem Cells*, 15: 297-304 (1997).
Pearson et al., "Methods for Derivation and Detection of Anti-Parasite Monoclonal Antibodies," Journal of Immunological Methods, 34 (1980) 141-154.
Pedersen, R. A., "Embryonic stem cells for medicine," *Sci. Amer*, 280: 68-73 (1999).
Photonic Instruments, Inc.; Micro Point-Laser System for Bio-Medical and Life Sciences; Product Information Sheet, Apr. 1996.
Pinkel et al., "High resolution analysis of DNA variation using comparative genomic hybridization to microarrays." Nat Genet. (1998) 20(2):207-11.
Powell et al., "Gel Microdroplets and Flow Cytometry: Rapid Determination of Antibody Secretion by Individual Cells Within A Cell Population," Nature Publishing Group, Bio/Technology vol. 9 (Apr. 1990).
Quiagen, "RNesay Midi/ Maxi Handbook Second Edition." Online (2001) 1-108.
Rill et al., "Direct Demonstration that Autologous Bone Marrow Transplantation for Solid Tumors Can Return a Multiplicity of Tumorigenic Cells," Blood, ; 84: 380-383 (1994).
Robertson et al. "Human Bone Marrow Depleted of CD33-Positive Cells Mediates Delayed but Durable Reconstitution of Hematopoiesis: Clinical Trial of MY( Monoclonal Antibody-Purged Autografts for the Treatment of Acute Myeloid Leukemia," Blood, 79(9):2229-2236 (1992).
Rowley, Scott D., "Pharmacological Purging of Malignant Cells; Bone Marrow Transplantation," *Boston-Blackwell Scientific Publications*, 164-178 (1994).
Sagi, et al. "Gene delivery into prostate cancer cells by holmium laser application." Prostate Cancer and Prostatic Diseases, 6: 127-130 (2003).
Schulze et al., "Tumor cell contamination of peripheral blood stem cell transplants and bone marrow in high-risk breast cancer patients," *Bone Marrow Transplant.*, 19: 1223-1228 (1997).
Schutze et al., "Identification of expressed genes by laser-mediated manipulation of single cells," *Nature Biotechnol.*, 16: 737-742 (1998).
Sharp et al., Significance of detection of occult Non-Hodgkin's Lymphoma in histologically uninvolved bone marrow by a culture technique, *Blood*, 79: 1074-1080 (1992).
Sharp et al., "Outcome of high-dose therapy and autologous transplantation in non-Hodgkin's lymphoma based on the presence of tumor in the marrow or infused hematopoietic harvest," *J. Clin. Oncol.*, 14: 214-219 (1996).
Shirahata, et al. "New technique for gene transfection using laser irradiation." J.Invest.Med., 49: 184-190 ( 2001).
Slebos et al.,"K-ras oncogene activation as a prognostic marker in adenocarcinoma of the lung" N. Engl. J. Med. (1990) 323: 561-565.
Smirnov et al., "Global Gene Expression Profiling of Circulating Tumor Cells." Cancer Res. (2005) 65(12):4993-7.
Soughayer, et al. "Characterization of cellular optoporation with distance." Anal.Chem., 72: 1342-1347 (2000).
Tao, et al. "Direct gene transfer into human cultured cells facilitated by laser micropuncture of the cell membrane." PNAS, 84: 4180-4184 (1987).
Theocharous et al., "The Detection and Genetic Analysis of Low Frequency Epithelial Tumor Cells in Patients with Breast Cancer," Blood, 88: 252a, Abstract 998, 441-II (1996).
Theriot et al., "Comparison of Actin and Cell Surface Dynamics in Motile Fibroblasts," J. Cell Biol., 119(2):367-377 (1992).
Thomas et al., "Direct Purging of Breast Carcinoma Cells with Anti-CD24 and/or Anti-Breast Carcinoma Antibodies Using a Novel Immunomagnetic Cell Depletion System," *Blood*, 88: 252a, Abstract 997, 440-II (1996).
Tirlapur, et al. "Targeted transfection by femtosecond laser." Nature, 418: 290-291 (2002).
Tricot et al., $CD34^+Thy^+lin^-$ peripheral blood stem cells (PBSC) effect timely trilineage engraftment in multiple Myeloma (MM), *Blood*, 86: 293a-0 (1995).
Tsukakoshi, et al. "A novel method of DNA transfection by laser microbeam cell surgery." Appl. Phys. B. 35: 135-140 (1984).
Turkevich et al., "A Study of the Nucleation and Growth Processes in the Synthesis of Colloidal Gold." Discuss. Faraday. Soc. (1951), 11, 55-75.
Vannucchi et al., "Evaluation of breast Tumor cell contamination in the bone marrow and leukapheresis collections by RT-PCR for cytokeratin-19 mRNA," *Br. J. Haematol*, 103: 610-617 (1998).
Vervoordeldonk et al., PCR-positivity in harvested bone marrow predicts relapse after transplantation with autologous purged bone marrow in children in second remission of precursor B-cell acute leukemia, *Br. J. Haematol.*, 96: 395-402 (1997).
Vredenburgh et al., "The significance of tumor contamination in the bone marrow from high-risk primary breast cancer patients treated with high-dose chemotherapy and hematopoietice support," *Biol. Blood Marrow Transplant.*, 3: 91-97 (1997).
Wagner et al., "Isolation of Small, Primitive Human Hematopoietic Stem Cells: Distribution of Cell Surface Cytokine Receptors and Growth in SCID-Hu Mice", Blood 86(2):512-523 (1995).
Yan et al., "Dissecting Complex Epigenetic Alterations in Breast Cancer Using CpG Island Microarrays." Cancer Res. (2001) 1;61(23):8375-80.
Young, WS 3rd. "In Situ Hybridization Histochemical Detection of Neuropeptide mRNA Using DNA and RNA Probes." Methods Enzymol. (1989) 168:702-10.
International Search Report dated Jul. 7, 1998 from PCT/US98/06125.
International Preliminary Examination Report dated Jan. 14, 1999 from PCT/US98/06125.
International Search Report dated Mar. 23, 2001 from PCT/US00/32742.
Written Opinion dated Nov. 6, 2001 from PCT/US00/32742.
International Preliminary Examination Report dated May 14, 2002 from PCT/US00/32742.

(56) References Cited

OTHER PUBLICATIONS

International Search Report dated Jan. 31, 2003 from PCT/US02/28755.
Written Opinion dated Dec. 1, 2003 from PCT/US02/28755.
Reply to Written Opinion dated Dec. 31, 2003 from PCT/US02/28755.
International Search Report dated Jun. 6, 2001 from PCT/US01/07506.
Written Opinion dated Dec. 27, 2001 from PCT/US01/07506.
International Preliminary Examination Report dated May 8, 2002 from PCT/US01/07506.
International Search Report and Written Opinion dated May 3, 2005 from PCT/US04/035803.
International Preliminary Examination Report dated May 11, 2006 from PCT/US04/035803.
International Search Report and Written Opinion dated Jun. 10, 2005 from PCT/US05/008347.
International Preliminary Examination Report dated Sep. 28, 2006 from PCT/US05/008347.
International Search Report and Written Opinion dated Jun. 25, 2010 from PCT/US2010/020562.
International Search Report dated Jun. 28, 2002 from PCT US01/50646.
Written Opinion dated Mar. 6, 2003 from PCT/US01/50646.
International Preliminary Examination Report dated Aug. 7, 2003 from PCT/US01/50646.
Office Action dated Jan. 2, 1998 in U.S. Appl. No. 08/824,968.
Applicant's Response to Office Action dated Mar. 23, 1998 in U.S. Appl. No. 08/824,968.
Office Action dated Jun. 17, 1998 in U.S. Appl. No. 08/824,968.
Applicant's Response to Office Action dated Sep. 8, 1998 in U.S. Appl. No. 08/824,968.
Notice of Allowance and Interview Summary dated Sep. 29, 1998 in U.S. Appl. No. 08/824,968.
Preliminary Amendment dated Sep. 29, 1999 in U.S. Appl. No. 09/049,677.
Office Action dated Jan. 12, 2000 in U.S. Appl. No. 09/049,677.
Applicant's Response to Office Action dated Mar. 9, 2000 in U.S. Appl. No. 09/049,677.
Notice of Allowance dated May 12, 2000 in U.S. Appl. No. 09/049,677.
Office Action dated Jan. 26, 2001 in U.S. Appl. No. 09/451,659.
Applicant's Response to Office Action dated Feb. 23, 2001 in U.S. Appl. No. 09/451,659.
Office Action dated Apr. 11, 2001 in U.S. Appl. No. 09/451,659.
Applicant's Response to Office Action dated Jul. 10, 2001 in U.S. Appl. No. 09/451,659.
Office Action dated Aug. 29, 2001 in U.S. Appl. No. 09/451,659.
Applicant's Response to Office Action dated Nov. 28, 2001 in U.S. Appl. No. 09/451,659.
Office Action dated Mar. 13, 2002 in U.S. Appl. No. 09/451,659.
Interview Summary dated May 13, 2002 in U.S. Appl. No. 09/451,659.
Interview Summary dated Jun. 3, 2002 in U.S. Appl. No. 09/451,659.
Applicant's Response to Office Action dated Jul. 9, 2002 in U.S. Appl. No. 09/451,659.
Notice of Allowability dated Jul. 29, 2002 in U.S. Appl. No. 09/451,659.
Office Action dated Apr. 24, 2001 in U.S. Appl. No. 09/728,281.
Applicant's Response to Office Action dated Jul. 23, 2001 in U.S. Appl. No. 09/728,281.
Office Action dated Oct. 5, 2001 in U.S. Appl. No. 09/728,281.
Applicant's Response to Office Action dated Jan. 3, 2002 in U.S. Appl. No. 09/728,281.
Office Action dated Apr. 23, 2002 in U.S. Appl. No. 09/728,281.
Applicant's Response to Office Action dated Jul. 23, 2002 in U.S. Appl. No. 09/728,281.
Applicant's Communication dated Aug. 14, 2002 in U.S. Appl. No. 09/728,281.
Interview Summary dated Aug. 14, 2002 in U.S. Appl. No. 09/728,281.
Notice of Allowance and Examiner's Amendment dated Aug. 28, 2002 in U.S. Appl. No. 09/728,281.
Amendment under § 1.312 dated Nov. 27, 2002 in U.S. Appl. No. 09/728,281.
Office Communication dated Dec. 4, 2002 in U.S. Appl. No. 09/728,281.
Preliminary Amendment dated Aug. 21, 2006 in U.S. Appl. No. 10/814,966.
Office Action dated Oct. 5, 2006 in U.S. Appl. No. 10/814,966.
Applicant's Response to Office Action dated Nov. 2, 2006 in U.S. Appl. No. 10/814,966.
Office Action dated Jan. 31, 2007 in U.S. Appl. No. 10/814,966.
Applicant's Response to Office Action and Terminal Disclaimer dated Feb. 22, 2007 in U.S. Appl. No. 10/814,966.
Notice of Allowance dated Jun. 4, 2007 in U.S. Appl. No. 10/814,966.
Applicant's Amendment under § 1.312 dated Sep. 4, 2007 in U.S. Appl. No. 10/814,966.
Entering of § 1.312 Amendment dated Oct. 9, 2007 in U.S. Appl. No. 10/814,966.
Office Action dated Oct. 25, 2001 in U.S. Appl. No. 09/665,545.
Applicant's Response to Office Action dated Apr. 25, 2002 in U.S. Appl. No. 09/665,545.
Office Action dated Jul. 9, 2002 in U.S. Appl. No. 09/665,545.
Preliminary Amendment dated Mar. 27, 2003 in U.S. Appl. No. 10/341,333.
Preliminary Amendment dated Sep. 22, 2004 in U.S. Appl. No. 10/341,333.
Office Action dated Sep. 21, 2005 in U.S. Appl. No. 10/341,333.
Applicant's Response to Office Action dated Mar. 17, 2006 in U.S. Appl. No. 10/341,333.
Terminal Disclaimer dated Jun. 9, 2006 in U.S. Appl. No. 10/341,333.
Notice of Allowance and Examiner's Amendment dated Jul. 7, 2006 in U.S. Appl. No. 10/341,333.
Examiner's Amendment dated Aug. 25, 2006 in U.S. Appl. No. 10/341,333.
Office Action dated Apr. 19, 2001 in U.S. Appl. No. 09/524,164.
Applicant's Response to Office Action dated May 18, 2001 in U.S. Appl. No. 09/524,164.
Office Action dated Jun. 20, 2001 in U.S. Appl. No. 09/524,164.
Applicant's Response to Office Action dated Oct. 19, 2001 in U.S. Appl. No. 09/524,164.
Office Action dated Jan. 30, 2002 in U.S. Appl. No. 09/524,164.
Interview Summary dated Jun. 19, 2002 in U.S. Appl. No. 09/524,164.
Applicant's Response to Office Action dated Jul. 1, 2002 in U.S. Appl. No. 09/524,164.
Interview Summary dated Feb. 10, 2003 in U.S. Appl. No. 09/524,164.
Notice of Allowance and Examiner's Amendment dated Feb. 13, 2003 in U.S. Appl. No. 09/524,164.
Amendment After Allowance under § 1.312 dated May 12, 2003 in U.S. Appl. No. 09/524,164.
Entering of § 1.312 Amendment dated Jun. 17, 2003 in U.S. Appl. No. 09/524,164.
Office Action dated Mar. 24, 2005 in U.S. Appl. No. 10/698,343.
Applicant's Response to Office Action dated Apr. 22, 2005 in U.S. Appl. No. 10/698,343.
Office Action dated May 13, 2005 in U.S. Appl. No. 10/698,343.
Applicant's Response to Office Action dated Nov. 14, 2005 in U.S. Appl. No. 10/698,343.
Interview Summary dated Jan. 27, 2006 in U.S. Appl. No. 10/698,343.
Office Action dated Jan. 27, 2006 in U.S. Appl. No. 10/698,343.
Pre-Appeal Brief Request for Review and Notice of Appeal dated Jul. 27, 2006 submitted by Applicant in U.S. Appl. No. 10/698,343.
Notice of Panel Decision dated Sep. 6, 2006 in U.S. Appl. No. 10/698,343.
Preliminary Amendment dated Nov. 25, 2005 in U.S. Appl. 10/801,931.
Office Action dated Jun. 9, 2006 in U.S. Appl. No. 10/801,931.

(56) References Cited

OTHER PUBLICATIONS

Applicant's Response to Office Action dated Nov. 9, 2006 in U.S. Appl. No. 10/801,931.
Office Action dated Jan. 18, 2007 in U.S. Appl. No. 10/801,931.
Interview Summary dated Apr. 23, 2007 in U.S. Appl. No. 10/801,931.
Applicant's Response to Office Action dated Jun. 18, 2007 in U.S. Appl. No. 10/801,931.
Notice of Allowance and Interview Summary dated Jul. 18, 2007 in U.S. Appl. No. 10/801,931.
Applicant's Request for Continued Examination dated Sep. 25, 2007 in U.S. Appl. No. 10/801,931.
Notice of Allowance dated Nov. 2, 2007 in U.S. Appl. No. 10/801,931.
Preliminary Amendment dated Aug. 15, 2002 in U.S. Appl. No. 09/961,691.
Office Action dated Dec. 23, 2002 in U.S. Appl. No. 09/961,691.
Applicant's Response to Office Action and Declaration Affidavits dated Apr. 23, 2003 in U.S. Appl. No. 09/961,691.
Office Action and Interview Summary dated Jul. 16, 2003 in U.S. Appl. No. 09/961,691.
Applicant's Response to Office Action, Request for Continued Examination, and Terminal Disclaimer dated Oct. 16, 2003 in U.S. Appl. No. 09/961,691.
Notice of Allowance and Interview Summary dated Dec. 18, 2003 in U.S. Appl. No. 09/961,691.
Applicant's Amendment after Notice of Allowance under § 1.312 dated Mar. 3, 2004 in U.S. Appl. No. 09/961,691.
Preliminary Amendment dated Mar. 18, 2003 in U.S. Appl. No. 10/392,636.
Office Action dated Feb. 2, 2009 in U.S. Appl. No. 11/894,720.
Office Action dated Apr. 3, 2008 in U.S. Appl. No. 11/842,112.
Preliminary Amendment dated Sep. 22, 2004 in U.S. Appl. No. 10/359,483.
Office Action dated Sep. 21, 2005 in U.S. Appl. No. 10/359,483.
Applicant's Response to Office Action dated Oct. 20, 2005 in U.S. Appl. No. 10/359,483.
Office Action dated Jul. 21, 2006 in U.S. Appl. No. 10/359,483.
Applicant's Response to Office Action dated Nov. 3, 2006 in U.S. Appl. No. 10/359,483.
Office Action dated Jan. 25, 2007 in U.S. Appl. No. 10/359,483.
Applicant's Response to Office Action and Interview Summary dated Jun. 25, 2007 in U.S. Appl. No. 10/359,483.
Applicant's Request for Continued Examination and Office Action Response dated Jul. 18, 2007 in U.S. Appl. No. 10/359,483.
Office Action dated Oct. 10, 2007 in U.S. Appl. No. 10/359,483.
Applicant's Response to Office Action dated Jan. 10, 2008 in U.S. Appl. No. 10/359,483.
Office Action dated Apr. 21, 2008 in U.S. Appl. No. 10/359,483.
Applicant's Response to Office Action dated Aug. 20, 2008 in U.S. Appl. No. 10/359,483.
Applicant's Response to Notice of Non-Compliant Amendment dated Sep. 18, 2008 in U.S. Appl. No. 10/359,483.
Notice of Allowance dated Dec. 24, 2008 in U.S. Appl. No. 10/359,483.
Preliminary Amendment dated Aug. 6, 2007 in U.S. Appl. No. 11/711,426.
Preliminary Amendment dated Oct. 1, 2008 in U.S. Appl. No. 11/711,426.
Office Action dated Mar. 26, 2010 in U.S. Appl. No. 11/711,426.
Applicant's Response to Office Action dated Sep. 20, 2010 in U.S. Appl. No. 11/711,426.
Office Action dated Nov. 9, 2010 in U.S. Appl. No. 11/711,426.
Office Action dated Apr. 4, 2008 in U.S. Appl. No. 11/842,090.
Applicant's Response to Office Action dated Oct. 3, 2008 in U.S. Appl. No. 11/842,090.
Office Action dated Nov. 4, 2008 in U.S. Appl. No. 11/842,090.
Applicant's Notice of Appeal dated May 4, 2009 in U.S. Appl. No. 11/842,090.
Applicant's Request for Continued Examination, Response to Office Action, and Terminal Disclaimer filed Aug. 13, 2009 in U.S. Appl. No. 11/842,090.
Notice of Allowance dated Sep. 9, 2009 in U.S. Appl. No. 11/842,090.
Office Action dated Aug. 19, 2010 in U.S. Appl. No. 12/533,801.
Notice of Allowance dated Oct. 7, 2010 in U.S. Appl. No. 12/405,875.
Preliminary Amendment dated Mar. 25, 2010 in U.S. Appl. No. 12/684,854.
Preliminary Amendment dated Apr. 5, 2010 in U.S. Appl. No. 12/686,359.
Office Action dated Oct. 14, 2010 in U.S. Appl. No. 12/603,413.
Applican'ts Response to Office Action dated Apr. 4, 2011 in U.S. Appl. No. 12/603,413.
Office Action dated May 2, 2011 in U.S. Appl. No. 12/603,413.
Office Action dated Oct. 27, 2003 in U.S. Appl. No. 10/037,478.
Applicant's Response to Office Action dated Feb. 23, 2004 in U.S. Appl. No. 10/037,478.
Notice of Allowance dated May 13, 2004 in U.S. Appl. No. 10/037,478.
Office Action dated Dec. 3, 2009 in U.S. Appl. No. 12/420,756.
Response to Office Action dated Jun. 3, 2010 in U.S. Appl. No. 12/420,756.
Office Action dated Jul. 1, 2010 in U.S. Appl. No. 12/420,756.
Response to Office Action dated Nov. 1, 2010 in U.S. Appl. No. 12/420,756.
Notice of Allowance dated Nov. 18, 2010 in U.S. Appl. No. 12/420,756.
Office Action dated Feb. 3, 2005 in U.S. Appl. No. 10/952,152.
Response to Office Action dated Jul. 25, 2005 in U.S. Appl. No. 10/952,152.
Final Office Action dated Sep. 30, 2005 in U.S. Appl. No. 10/952,152.
Notice of Appeal and Response dated Mar. 28, 2006 in U.S. Appl. No. 10/952,152.
Notice of Allowance dated Apr. 20, 2006 in U.S. Appl. No. 10/952,152.
Communication dated Sep. 13, 2000 in AU patent application No. 67826/98.
Applicant's Response to Communication dated Sep. 11, 2001 in AU patent application No. 67826/98.
Communication dated Oct. 8, 2001 in AU patent application No. 67826/98.
Applicant's Response to Communication dated Nov. 20, 2001 in AU patent application No. 67826/98.
Communication dated Sep. 4, 2007 in CA patent application No. 2281112.
Applicant's Response to Communication dated Feb. 23, 2009 in CA patent application No. 2281112.
Communication dated Jun. 10, 2010 in CA patent application No. 2281112.
Applicant's Response to Communication dated Dec. 9, 2010 in CA patent application No. 2281112.
Communication dated Jul. 12, 2002 in CN patent application No. 98803760.2.
Applicant's Response to Communication dated Nov. 18, 2002 in CN patent application No. 98803760.2.
Communication dated Apr. 30, 2003 in CN patent application No. 98803760.2.
Applicant's Response to Communication dated Aug. 11, 2003 in CN patent application No. 98803760.2.
Communication dated Sep. 17, 2003 in CN patent application No. 98803760.2.
Communication dated Nov. 24, 2003 in CN patent application No. 98803760.2.
Grant dated Jun. 18, 2004 in CN patent application No. 98803760.2.
Communication dated Oct. 7, 2002 in EP patent application No. 98913223.8.
Communication dated Mar. 5, 2003 in EP patent application No. 98913223.8.
Applicant's Response to Communication dated Sep. 15, 2003 in EP patent application No. 98913223.8.

(56) References Cited

OTHER PUBLICATIONS

Communication dated Aug. 27, 2004 in EP patent application No. 98913223.8.
Communication dated Jan. 12, 2005 in EP patent application No. 98913223.8.
Applicant's Response to Communication dated Jul. 11, 2005 in EP patent application No. 98913223.8.
Communication dated Oct. 18, 2005 in EP patent application No. 98913223.8.
Applicant's Response to Communication dated Jan. 5, 2006 in EP patent application No. 98913223.8.
Grant dated Dec. 27, 2006 in EP patent application No. 98913223.8.
Communication dated Sep. 30, 2008 in JP patent application No. 543286/1998.
Applicant's Response to Communication dated Jan. 16, 2009 in JP patent application No. 543286/1998.
Communication dated Apr. 21, 2009 in JP patent application No. 543286/1998.
Applicant's Response to Communication dated Sep. 10, 2009 in JP patent application No. 543286/1998.
Grant dated Apr. 27, 2010 in JP patent application No. 543286/1998.
Communication dated Nov. 30, 2001 in KR patent application No. 99-7007829.
Applicant's Response to Communication dated Feb. 20, 2002 in KR patent application No. 99-7007829.
Communication dated Jun. 27, 2003 in KR patent application No. 99-7007829.
Communication dated Jul. 15, 2002 in MX patent application No. 998715.
Applicant's Response to Communication dated Sep. 19, 2002 in MX patent application No. 998715.
Communication dated Jun. 10, 2003 in MX patent application No. 998715.
Communication dated Feb. 23, 2005 in AU patent application No. 19392/01.
Applicant's Response to Communication dated Jul. 24, 2006 in AU patent application No. 19392/01.
Communication dated Aug. 10, 2006 in AU patent application No. 19392/01.
Applicant's Response to Communication dated Nov. 10, 2006 in AU patent application No. 19392/01.
Communication dated Jun. 10, 2008 in CA patent application No. 2392534.
Applicant's Response to Communication dated Dec. 9, 2008 in CA patent application No. 2392534.
Communication dated Jun. 9, 2010 in CA patent application No. 2392534.
Communication dated Nov. 12, 2002 in EP patent application No. 00982344.4.
Communication dated May 29, 2006 in EP patent application No. 00982344.4.
Applicant's Response to Communication dated Mar. 20, 2007 in EP patent application No. 00982344.4.
Communication dated Dec. 13, 2007 in EP patent application No. 00982344.4.
Applicant's Response to Communication dated May 2, 2008 in EP patent application No. 00982344.4.
Communication dated Dec. 9, 2009 in EP patent application No. 00982344.4.
Applicant's Response to Communication dated May 6, 2010 in EP patent application No. 00982344.4.
Communication dated Oct. 1, 2010 in EP patent application No. 10175331.7.
Communication dated Sep. 13, 2006 in AU patent application No. 2002333551.
Applicant's Response to Communication dated Jun. 26, 2007 in AU patent application No. 2002333551.
Communication dated Jan. 22, 2009 in EP patent application No. 02799574.5.
Communication dated Sep. 25, 2009 in EP patent application No. 02799574.5.
Communication dated Jun. 17, 2008 in JP patent application No. 2003-530796.
Applicant's Response to Communication dated Dec. 16, 2008 in JP patent application No. 2003-530796.
Communication dated Feb. 19, 2010 in JP patent application No. 2003-530796.
Communication dated Jun. 12, 2006 in EP patent application No. 1916503.4.
Communication dated Oct. 25, 2006 in EP patent application No. 1916503.4.
Communication dated Oct. 10, 2008 in CN patent application No. 200480031867.8.
Applicant's Response to Communication dated Mar. 25, 2009 in CN patent application No. 200480031867.8.
Communication dated Mar. 18, 2010 in CN patent application No. 200480031867.8.
Communication dated Mar. 5, 2008 in EP patent application No. 4796645.2.
Applicant's Response to Communication dated Dec. 22, 2008 in EP patent application No. 4796645.2.
Communication dated Mar. 29, 2010 in EP patent application No. 4796645.2.
Applicant's Response to Communication dated Oct. 4, 2010 in EP patent application No. 4796645.2.
Communication dated Dec. 20, 2006 in EP patent application No. 5727754.3.
Applicant's Response to Communication dated May 25, 2007 in EP patent application No. 5727754.3.
Grant dated May 21, 2008 in EP patent application No. 5727754.3.
Communication dated Jul. 27, 2010 in JP patent application No. 2001-542522.
Applicant's Response to Communication dated Oct. 27, 2010 in JP patent application No. 2001-542522.
Communication dated Jan. 28, 2010 in CA patent application No. 2461611.
Communication dated Nov. 30, 2009 in AU patent application No. 2004286834.
Communication dated Jul. 27, 2010 in JP patent application No. 2006-538243.
Communication dated Jun. 10, 2009 in AU patent application No. 2005224624.
Applicant's Response to Communication dated Oct. 28, 2009 in AU patent application No. 2005224624.
Communication dated Nov. 24, 2009 in AU patent application No. 2005224624.
Grant dated Mar. 14, 2010 in AU patent application No. 2005224624.
Communication dated Oct. 26, 2010 in JP patent application No. 2007-503988.
Communication dated Jan. 28, 2010 in CA application No. 2426871.
Communication dated Dec. 2, 2008 in JP application No. 2008-137319.
Applicant's Response to Communication dated Jun. 1, 2009 in JP application No. 2008-137319.
Communication dated Mar. 3, 2010 in JP application No. 2008-137319.
Communication dated Jun. 6, 2010 in JP application No. 2008-137319.
Communication dated Nov. 26, 2007 in JP application No. 2002-540540.
Applicant's Response to Communication dated May 26, 2008 in JP application No. 2002-540540.
Communication dated Jun. 17, 2008 in JP application No. 2002-540540.
Applicant's Response to Communication and Notice of Appeal dated Sep. 16, 2008 in JP application No. 2002-540540.
Communication dated Nov. 30, 2010 in JP patent application No. 2002-540540.
Communication dated Oct. 9, 2006 in AU patent application No. 2002232892.

(56) References Cited

OTHER PUBLICATIONS

Applicant's Response to Communication dated Jun. 2, 2008 in AU patent application No. 2002232892.
Patent Grant dated Oct. 9, 2008 in AU patent application No. 2002232892.
Communication dated Nov. 5, 2008 in EP patent application No. 01 992 423.2.
Communication dated Feb. 26, 2009 in EP patent application No. 01 992 423.2.
Applicant's Response to Communication dated Sep. 1, 2009 in EP patent application No. 01 992 423.2.

* cited by examiner

Ebs from LEAP passaged iPSCs

Ebs from Collagenase passaged iPSCs

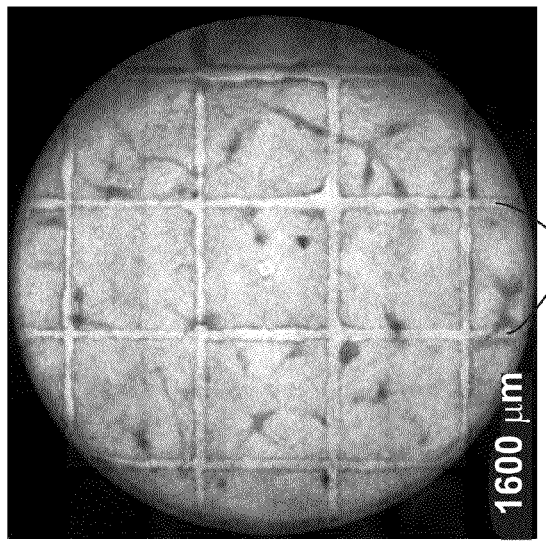
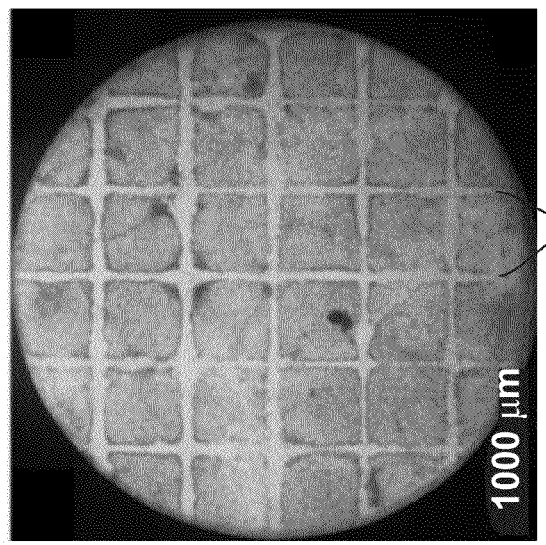
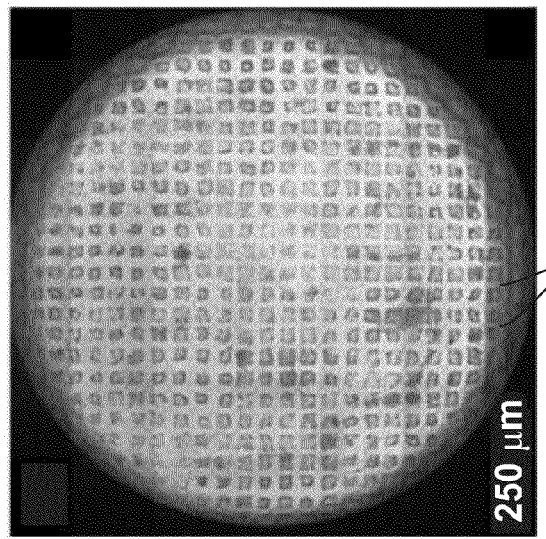
FIG. 15C
FIG. 15B
FIG. 15A

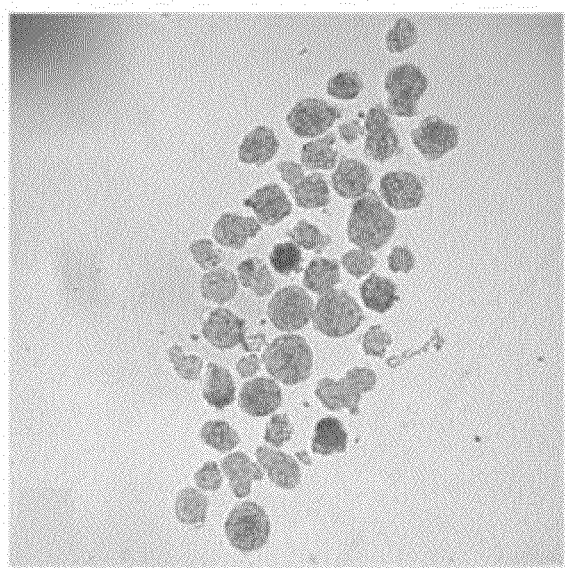
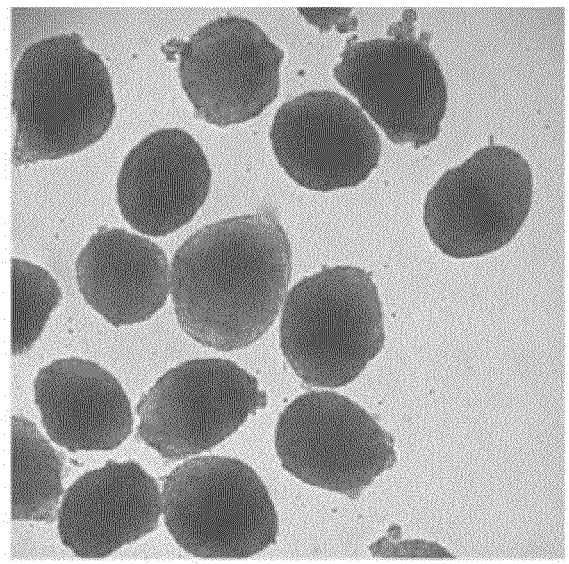
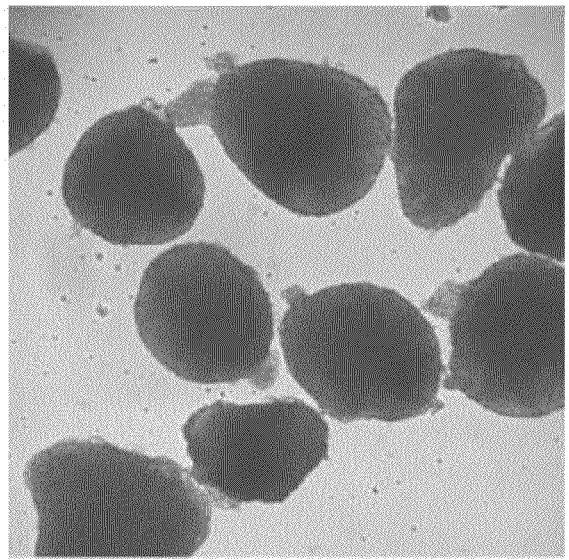
FIG. 16A
FIG. 16B
FIG. 16C

LASER MEDIATED SECTIONING AND TRANSFER OF CELL COLONIES

CROSS-REFERENCE TO RELATED APPLICATIONS

The present application claims priority to U.S. Provisional Application No. 61/144,101, filed on Jan. 12, 2009, entitled LASER MEDIATED SECTIONING AND TRANSFER OF CELL COLONIES, which is incorporated herein by reference in its entirety.

BACKGROUND

Recently, interest in cellular technologies, particularly stem cells has increased. In the case of stem cells, the interest can be attributed to the potential of stem cells to provide new understanding into biological processes and to provide new and improved therapies for a variety of conditions.

Stem cells have the potential to develop into many different cell types in the body. Serving as a sort of repair system for the body, they can theoretically divide without limit to replenish other cells as long as the person or animal is still alive. When a stem cell divides, each new cell has the potential to either remain a stem cell or become another type of cell with a more specialized function, such as a muscle cell, a red blood cell, or a brain cell. Thus, there is high interest in developing stem cell and other cellular technologies, and as a result, an increased demand for improved culturing techniques.

Certain types of cell cultures, including many stem cells, grow into colonies. To increase growth, those culturing the cells often desire to section (i.e., to fragment, divide, or break up) the colonies into uniform or semi-uniform sub colonies of cells. Known methods for achieving sectioning often involve manual slicing of colonies using a straight edge or addition of a chemical. These methods often damage significant numbers of cells in the colonies and are not sufficiently fast for high throughput applications. Discussed herein are methods and devices for improving speed and efficacy of sectioning techniques for cell colonies and whole cultures.

SUMMARY

The systems, methods, and devices of described herein each may have several aspects, no single one of which is solely responsible for its desirable attributes. Without limiting the scope of this disclosure as expressed by the claims which follow, its more prominent features will now be discussed briefly. After considering this discussion, and particularly after reading the section entitled "Detailed Description" one will understand how the features of this technology provide advantages.

In one aspect, a method of sectioning a cell colony can include, for example, providing a living cell colony on a surface; imaging the cell colony; selecting a specific colony for sectioning based upon a desired phenotype for the colony, which phenotype can be identified in the image (for example, cells exhibiting the phenotype can be identified using the image); identifying at least a portion of the edge of the specific colony in the image; applying electromagnetic radiation to the identified edge of the specific colony to separate the specific colony from rest of the cell colonies; and sectioning the specific colony into one or more sub colony pieces using electromagnetic radiation. In the context of this disclosure, the term "colony" is intended to mean a grouping of closely associated cells, where the term "sub colony" is intended to mean a smaller grouping of closely associated cells that is derived from a larger colony that is sectioned. A large colony may therefore be sectioned or divided into multiple sub colonies or pieces of closely associated cells.

In another aspect, a method of sectioning a cell colony can include, for example, providing a living cell colony on a surface; imaging the cell colony; selecting a specific colony exhibiting a desired phenotype, which phenotype is identified in the image (for example, cells exhibiting the phenotype can be identified using the image); and sectioning the colony into one or more pieces using a pattern of electromagnetic cutting lines.

In another aspect, a method of sectioning a cell colony can include, for example, providing a cell colony on a surface; imaging the cell colony; segmenting the imaged cell colony with a pattern for electromagnetic radiation cutting lines; and applying electromagnetic radiation to the cell colony according to the segmented pattern of electromagnetic radiation cutting lines to section the cell colony into one or more pieces.

In another aspect, a method of sectioning a cell colony can include, for example, providing a cell colony on a culture surface; locating the optimal focal position of the actual culture surface using automated focus technology without knowledge of the bottom thickness; positioning the culture surface at the optimal focal position for sectioning; and sectioning a portion or all of the entire culture into one or more pieces using a pattern of laser cutting lines.

In another aspect, a method of sectioning a cell colony can include, for example, providing a living cell colony on a surface; imaging the cell colony; selecting a specific colony for sectioning based upon a desired phenotype for the colony, which phenotype can be identified in the image (for example, cells exhibiting the phenotype can be identified using the image); identifying at least a portion of the edge of the specific colony in the image; applying electromagnetic radiation to the identified edge of the specific colony to separate the specific colony from rest of the cell colonies; and then applying electromagnetic radiation to the rest of the culture to eliminate all non-identified cells thereby isolating the specific colony.

In another aspect, a method of sectioning a cell colony can include, for example, providing a cell colony on a culture plate, which plate can include or have for example, a known bottom thickness; positioning the culture plate at an optimal focal position for laser cutting using automated focus technology to identify the underside of the bottom surface of the culture plate and applying an appropriate z-offset based on the known thickness of the bottom; and sectioning the cell colony into one or more pieces using a pattern of laser cutting lines that are focused at the optimal focal plane.

In another aspect, a method of sectioning a cell colony can include, for example, providing a cell colony on a culture surface; locating the optimal focal position of the culture surface using automated focus technology without knowledge of the bottom thickness; positioning the culture surface at the optimal focal position for sectioning; and sectioning a portion or all of the entire culture into one or more pieces using a pattern of laser cutting lines.

In some embodiments, the methods can include, for example, imaging a cell colony using transmitted light. In some embodiments, the transmitted light can be, for example, brightfield (BF). In some embodiments, the transmitted light can be, for example, phase contrast. In some embodiments, the transmitted light can be, for example, darkfield. In some embodiments, the transmitted light can be, for example, differential interference contrast. In some embodiments, the imaging of the cell colony can include, for example, imaging using fluorescence. In some embodiments, the sectioning of the colony can include, for example, defining the pattern of the laser cutting lines. In some embodiments, the sectioning of the colony into one or more pieces using a pattern of laser cutting lines can include, for example, a photothermal mechanism. In some embodiments, the photothermal mechanism can include, for example, adding a dye configured to absorb laser wavelength and cause an increase in temperature. In some embodiments, the photothermal mechanism may be configured to photocoagulate the cells in place. In some embodiments, the cells can be killed at a focal point of the laser. In some embodiments, the sectioning of the colony into one or more pieces using a pattern of laser cutting lines can include, for example, a photomechanical mechanism. In some embodiments, the photomechanical mechanism may involve physical destruction of the cells at a focal point of the laser. In some embodiments, the sectioning of the cell colony into one or more pieces using a pattern of laser cutting lines can include, for example, a photochemical mechanism. In some embodiments, the photochemical mechanism may use a UV laser to induce selective apoptosis at a focal plane of the laser. In some embodiments, the photomechanical, photothermal, and/or photochemical mechanisms can include addition of reagents to facilitate laser-mediated sectioning of cultures into one or more pieces. The laser may be a continuous wave laser, or a pulsed laser that delivers a series of high energy pulses.

In some embodiments, the cell colony can be contained in a multi-well device, for example a 1, 6, 12, 24, 48, 96 or 384 well plate.

In some embodiments, the method further can include, for example, removing the sectioned one or more pieces. In some embodiments, the removing of the sectioned one or more pieces can include, for example, dislodging the one or more pieces into suspension within the fluid of a first culture vessel. In some embodiments, the removing of the sectioned one or more pieces can include, for example, addition of chemicals, such as enzymes, prior to dislodging the one or more pieces into suspension within the fluid of the first culture vessel. In some embodiments, the method further can include, for example, transferring the one or more pieces to a second culture vessel. For example, in some aspects the second culture vessel can be a multi-well device such as a 1, 6, 12, 24, 48, 96 or 384 well plate. In some embodiments, the removing of the sectioned one or more pieces can include, for example, a fluid pipetting technique. In some embodiments, the fluid pipetting technique may be motorized. In some embodiments, the method further can include, for example, washing out the remaining feeder layer.

In some embodiments, the cell colony can include, for example, living embryonic stem (ES) or induced pluripotent stem (iPS) cells. In some embodiments, the cell colony may include, for example, ES cells. In some embodiments, the cell colony may include, for example, iPS cells. In some embodiments, the cell colony may include, for example, non-ES/iPS cells, such as tumor spheroids, embryoid bodies, neurospheres, embryonic germ cells, embryonic carcinoma cells, breast cancer stem cells, cancer stem cells, or any cell type that may form a collection of cells in a colony.

In some embodiments, the electromagnetic cutting pattern can include, for example, a grid pattern. In some embodiments, the pattern of electromagnetic cutting lines may be limited to the boundaries of the cell colony. In some embodiments, the method further can include, for example, segmenting the imaged cell colony prior to sectioning the colony.

In another aspect, a method of sectioning a cell colony includes, for example, providing a living cell colony on a culture surface; imaging the cell colony; selecting a colony for sectioning based upon a desired phenotype for the colony, which phenotype is shown in the image; identifying at least a portion of the edge of the colony in the image; applying electromagnetic radiation to the identified edge of the colony to separate the colony from rest of the culture; and sectioning the colony into one or more pieces using electromagnetic radiation.

In some embodiments, sectioning the colony includes, for example, defining the pattern of the laser cutting lines. In some embodiments, sectioning the colony includes, for example, the use of a series of laser pulses which may be emitted using a range of laser energies from about 1 to about 50 µJ per pulse. In some embodiments, sectioning the colony includes, for example, use of a series of laser pulses which may be emitted using a range of laser spot radii from about 1 to about 20 µm. In some embodiments, sectioning the colony includes, for example, use of a series of 532 nm laser pulses which may be emitted using 1 to 5 laser pulses. In some embodiments, sectioning the colony includes, for example, use of a series of approximately 532 nm laser pulses which may be emitted using between 1 and 5 laser repeats. In some embodiments, sectioning the colony includes, for example, a pattern of laser cutting lines with pulse spacing between about 5 to about 50 µm. In some embodiments, sectioning the colony includes, for example, a pattern of laser grids with grid spacing between about 5 to about 100 µm. In some embodiments, sectioning the colony includes, for example, a square pattern of laser cutting lines positioned about 20 to about 2000 µm. In some embodiments, sectioning the colony includes, for example, a square pattern of laser cutting lines positioned about 20 to about 300 µm apart for enzyme-free removal of sections. In some embodiments, sectioning the colony includes, for example, a square pattern of laser cutting lines positioned about 250 to about 2000 µm apart for use in differentiation of stem cells into mature specialized cell types. In some embodiments, sectioning the colony into one or more pieces using a pattern of laser cutting lines includes, for example, a photothermal mechanism. In some embodiments, the photothermal mechanism includes, for example, adding a dye configured to increase absorbance of the laser energy. In some embodiments, the photothermal mechanism is configured to photocoagulate the cells in place. In some embodiments, cells are killed at a focal point of the laser. In some embodiments, sectioning the colony into one or more pieces using a pattern of laser cutting lines includes, for example, a photomechanical mechanism. In some embodiments, the photomechanical mechanism involves physical destruction of the cells at a focal point of the laser. In some embodiments, sectioning the cell colony into one or more pieces using a pattern of laser cutting lines includes, for example, a photochemical mechanism. In some embodiments, the photochemical mechanism uses a UV laser to induce selective apoptosis at a focal plane of the laser.

In another aspect, a method of sectioning a cell colony, includes, for example, providing a living cell colony on a surface; imaging the cell colony; selecting a specific colony exhibiting a desired phenotype, which phenotype is identifiable in the image; and sectioning the colony into one or more pieces using a pattern of electromagnetic cutting lines.

In some embodiments, sectioning the colony includes, for example, defining the pattern of the laser cutting lines. In some embodiments, sectioning the colony into one or more pieces using a pattern of laser cutting lines includes, for example, a photothermal mechanism. In some embodiments, the photothermal mechanism includes, for example, adding a dye configured to increase absorbance of the laser energy. In some embodiments, the photothermal mechanism is configured to photocoagulate the cells in place. In some embodiments, sectioning the colony into one or more pieces using a pattern of laser cutting lines includes, for example, a photomechanical mechanism. In some embodiments, sectioning the colony into one or more pieces using a pattern of laser cutting lines includes, for example, a photochemical mechanism. In some embodiments, the photochemical mechanism uses a UV laser to induce selective apoptosis at a focal plane of the laser.

In another aspect, a method of sectioning a cell colony includes, for example, providing a cell colony on a surface; imaging the cell colony; segmenting the imaged cell colony with a pattern for electromagnetic radiation cutting lines; and applying electromagnetic radiation to the cell colony according to the segmented pattern of electromagnetic radiation cutting lines to section the cell colony into one or more pieces.

In some embodiments, sectioning the cell colony includes, for example, defining the pattern of the laser cutting lines. In some embodiments, sectioning the cell colony into one or more pieces using a pattern of laser cutting lines includes, for example, a photothermal mechanism. In some embodiments, the photothermal mechanism includes, for example, adding a dye configured to increase absorbance of the laser energy. In some embodiments, the photothermal mechanism is configured to photocoagulate the cells in place. In some embodiments, sectioning the cell colony into one or more pieces using a pattern of laser cutting lines includes, for example, a photomechanical mechanism. In some embodiments, sectioning the cell colony into one or more pieces using a pattern of laser cutting lines includes, for example, a photochemical mechanism. In some embodiments, the photochemical mechanism uses a UV laser to induce selective apoptosis at a focal plane of the laser.

In another aspect, a method of sectioning a cell colony includes, for example, providing a cell colony on a culture plate with a known thickness; positioning the culture plate at an optimal position for laser cutting using automated focus technology; and sectioning the cell colony into one or more pieces using a pattern of laser cutting lines.

In some embodiments, sectioning the cell colony includes, for example, defining the pattern of the laser cutting lines. In some embodiments, sectioning the cell colony into one or more pieces using a pattern of laser cutting lines includes, for example, a photothermal mechanism. In some embodiments, the photothermal mechanism includes, for example, adding a dye configured to increase the absorbance of the laser energy. In some embodiments, the photothermal mechanism is configured to photocoagulate the cells in place. In some embodiments, sectioning the cell colony into one or more pieces using a pattern of laser cutting lines includes, for example, a photomechanical mechanism. In some embodiments, sectioning the cell colony into one or more pieces using a pattern of laser cutting lines includes, for example, a photochemical mechanism. In some embodiments, the photochemical mechanism uses a UV laser to induce selective apoptosis at a focal plane of the laser.

In some embodiments the method further includes, for example, removing the sectioned one or more pieces. In some embodiments, removing the sectioned one or more pieces includes, for example, dislodging the one or more pieces into suspension within the fluid of a first culture vessel. In some embodiments, removing the sectioned one or more pieces includes, for example, addition of chemicals, such as enzymes, prior to dislodging the one or more pieces into suspension within the fluid of the first culture vessel.

In some embodiments the method further includes, for example, transferring the one or more pieces to a second culture vessel. In some embodiments, removing the sectioned one or more pieces includes, for example, a fluid pipetting technique. In some embodiments, the method further includes, for example, washing out remaining feeder layer. In some embodiments, the cell colony includes, for example, living embryonic or induced pluripotent stem cells. In some embodiments, the cell colony includes, for example, non-ES/iPS cells, tumor spheroids, or embryoid bodies, neurospheres, embryoid bodies, embryonic germ cells, embryonic carcinoma cells, breast cancer stem cells, cancer stem cells, and any cell type that may form a collection of like cells in a localized region. In some embodiments, the pattern includes, for example, a grid pattern. In some embodiments, the pattern of electromagnetic cutting lines is limited to the boundaries of the cell colony. In some embodiments the method further includes, for example, segmenting the imaged cell colony prior to sectioning the colony.

In another aspect a method of purifying a cell colony can include, for example, providing a living cell colony on a culture surface; optionally, applying electromagnetic radiation to an edge of the colony to separate the cell colony from rest of the culture; and applying electromagnetic radiation to at least a portion of the rest of the culture that is separated from the cell colony so as to purify the separated cell colony. In some optional aspects at least some or all of the rest of the culture can be separated from a cell colony without first separating the cell colony from the rest of the culture. In some aspects the electromagnetic radiation can be applied to about 50%-99.9% of the rest of the culture that has been separated or any number or range therebetween, for example. In some aspects, the electromagnetic radiation can be applied to all of the rest of the culture that has been separated from cell colony. In some embodiments, the electromagnetic radiation can be applied, for example, in a pattern. In some embodiments, the pattern can be a grid pattern for example.

In another aspect, a method of sectioning a cell colony may include, for example, providing a living cell colony on a culture surface; selecting a pattern of electromagnetic cutting lines; and applying the pattern of electromagnetic cutting lines to the cell culture surface so as to section the living cell colony into one or more pieces using electromagnetic radiation. In some aspects the cell colony can be part of a monolayer of cells, for example, stem cells.

Some embodiments relate to methods of sectioning a cell colony in a culture, which methods can include, for example, providing a living cell colony in a culture; imaging the culture; selecting a colony for sectioning based upon a desired phenotype for the colony, which phenotype is shown in the image; identifying at least a portion of the edge of the colony in the image; applying electromagnetic radiation to the identified edge of the colony to separate the colony from rest of the culture; and sectioning the colony into one or more pieces using electromagnetic radiation.

The applying electromagnetic radiation can include, for example, defining a pattern of laser cutting lines. The defining the pattern of laser cutting lines can include, for example, the use of a series of laser pulses which may be emitted using a range of laser energies from about 1 to about 50 µJ per pulse, for example. The defining the pattern of laser cutting lines may include, for example, use of a series of laser pulses which may be emitted using a range of laser spot radii from about 1 to about 20 µm. The defining the pattern of laser cutting lines may include, for example, use of a series of 532 nm laser pulses which may be emitted using 1 to 5 laser pulses. The defining the pattern of laser cutting lines can include, for example, use of a series of approximately 532 nm laser pulses which may be emitted using between 1 and 5 laser repeats.

The defining the pattern of laser cutting lines may include, for example, a pattern of laser cutting lines with pulse spacing between about 5 to about 50 μm. The defining the pattern of laser cutting lines may include, for example, a pattern of laser grids with grid spacing between about 5 to about 100 μm. The defining the pattern of laser cutting lines can include, for example, a square pattern of laser cutting lines positioned about 20 to about 2000 μm. The defining the pattern of laser cutting lines can include, for example, a square pattern of laser cutting lines positioned about 20 to about 300 μm apart for enzyme-free removal of sections. The defining the pattern of laser cutting lines may include, for example, a square pattern of laser cutting lines positioned about 250 to about 2000 μm apart for use in differentiation of stem cells into mature specialized cell types. The methods further can include, for example, adding a dye configured to increase absorbance of the electromagnetic radiation.

Also, some embodiments relate to methods of sectioning a cell colony, which methods can include for example, providing a living cell colony on a surface; imaging the surface; selecting a specific colony exhibiting a desired phenotype, which phenotype is identifiable in the image; and sectioning the colony into one or more pieces using a pattern of electromagnetic cutting lines.

The using a pattern of electromagnetic cutting lines can include, for example, defining a pattern of laser cutting lines. The methods further can include, for example, adding a dye configured to increase absorbance of the laser energy. The pattern can include, for example, a grid pattern. The pattern of electromagnetic cutting lines, in some aspects, can be limited to within the boundaries of the cell colony, for example. The methods further may include, for example, segmenting the imaged cell colony prior to sectioning the colony.

Some embodiments relate to methods of sectioning a cell colony, which methods can include for example, providing a cell colony on a surface; imaging the cell colony; segmenting the imaged cell colony; defining a pattern for electromagnetic radiation cutting lines; and applying electromagnetic radiation to the cell colony according to the defined pattern of electromagnetic radiation cutting lines to section the cell colony into one or more pieces.

The electromagnetic radiation cutting lines can comprise, for example, laser cutting lines. The methods further may include, for example, adding a dye configured to increase absorbance of the laser energy.

Still some embodiments relate to methods of sectioning a cell colony, which methods may include, for example, providing a cell colony on a culture surface comprising a known thickness; positioning the culture surface at an optimal focus position for laser cutting; and defining a pattern for electromagnetic radiation cutting lines wherein the pattern comprises the culture surface; sectioning the cell colony into one or more pieces using the pattern of laser cutting lines by applying electromagnetic radiation to the culture surface according to the pattern.

The methods further may include for example adding a dye configured to increase the absorbance of the laser energy. The methods further can include, for example, removing the sectioned one or more pieces. The removing the sectioned one or more pieces can include, for example, dislodging the one or more pieces into suspension within the fluid of a first culture vessel. The removing the sectioned one or more pieces can include, for example, addition of chemicals, such as enzymes, prior to dislodging the one or more pieces into suspension within the fluid of the first culture vessel. The methods further may include, for example, transferring the one or more pieces to a second culture vessel. The removing the sectioned one or more pieces can include, for example, the use of a fluid pipetting technique. The methods further may include, for example, washing out remaining feeder layer.

In the methods described herein the cell colony can include, for example, living embryonic or induced pluripotent stem cells. The cell colony may include, for example, non-ES/iPS cells, tumor spheroids, or embryoid bodies, neurospheres, embryoid bodies, embryonic germ cells, embryonic carcinoma cells, breast cancer stem cells, cancer stem cells, and any cell type that may form a collection of like cells in a localized region.

Some embodiments relate to methods of purifying a cell colony, which methods can include for example, providing a living cell colony on a culture surface; identifying a cell colony; applying electromagnetic radiation to an edge of the colony to isolate the cell colony from rest of the culture; and applying a pattern of electromagnetic radiation to kill the rest of the culture so as to purify the isolated cell colony.

Some embodiments relate to methods of purifying a cell colony, which methods can include for example, providing a living cell colony on a culture surface; identifying a cell colony; applying a pattern of electromagnetic radiation to the non-colony area of the culture to kill the rest of the culture, but not the cell colony.

Also, some embodiments relate to methods of sectioning a cell colony, which methods can include, for example, providing a living cell colony on a culture surface; defining a pattern of cutting lines; and applying electromagnetic energy in the pattern of the cutting lines at the culture surface so as to section the living cell colony into one or more pieces.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIGS. 15A, 15B, and 15C illustrate entire confluent iPS cell cultures sectioned into specific square section sizes (250, 1000, and 1600 µm squares, respectfully) with laser cutting lines 1510 that were applied without specifically identifying cell colonies and without regard to the edges of any colonies.

FIGS. 16A, 16B, and 16C illustrate the specifically sized embryoid bodies that formed from the entire cultures that were sectioned with the three sizes shown in FIGS. 15A, 15B, and 15C, respectfully.

DETAILED DESCRIPTION

Figure 1:
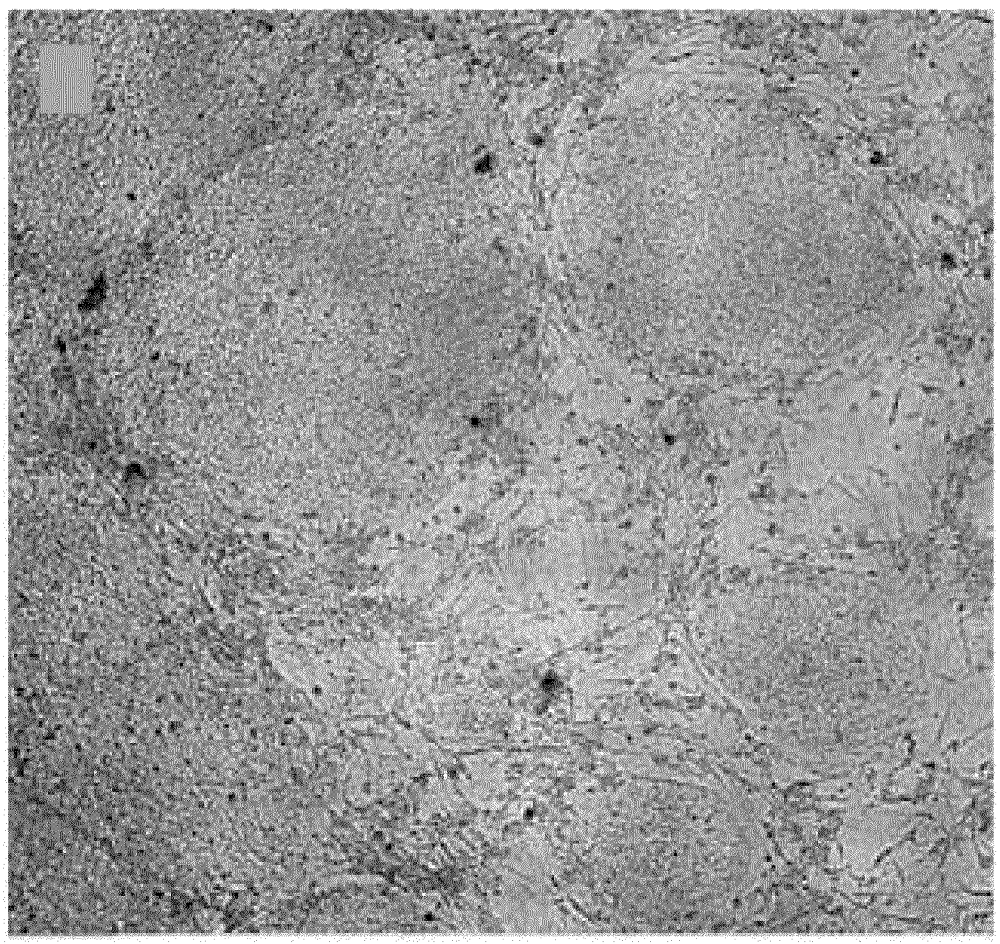
FIG. 1 illustrates living iPS cell colonies that exhibit a distinct textural contrast that can be distinguished from surrounding feeder cells or extracellular matrix.

The illustrative embodiments described in the detailed description, drawings, and claims are not meant to be limiting. The teachings herein can be applied in a multitude of different ways, including for example, as defined and covered by the claims. It should be apparent that the aspects herein may be embodied in a wide variety of forms and that any specific structure, function, or both being disclosed herein is merely representative. Based on the teachings herein one skilled in the art should appreciate that an aspect disclosed herein may be implemented independently of any other aspect and that two or more of these aspects may be combined in various ways. For example, systems, compositions, or apparatuses may be implemented or methods may be practiced by one of skill in the art using any reasonable number or combination of the aspects set forth herein. In addition, such a system, composition or apparatus may be implemented or such a method may be practiced using other structure, functionality, or structure and functionality in addition to or other than one or more of the aspects set forth herein. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and made part of this disclosure. It is to be understood that the disclosed embodiments are not limited to the examples described below, as other embodiments may fall within disclosure and the claims.

The recent dramatic increase in discoveries and financial support for stem cell biology, particularly embryonic stem (ES) and induced pluripotent stem (iPS) cell biology, for applications in discovery biology, drug discovery, and cell therapy has imposed considerable pressure to manage stem cells such as ES/iPS cells on a larger scale than currently possible. These cells can grow as tight aggregates either on a feeder layer of cells and/or a complex extracellular matrix coated surface. When the aggregates (or cell colonies) reach a certain size or density, the stem cells begin to differentiate and are thus no longer useful as stem cells, such as for example, ES/iPS cells.

To propagate stem cells such as ES/iPS cells in the cell colonies without differentiation, various methods have been developed to section the cell colonies (that have not yet grown to the point of differentiation) into smaller sub colony pieces so they may continue to proliferate as ES/iPS cells. Some of these methods use pipettes to forcibly break up cell colonies using the up and down motion of the liquid in the pipette. Some of the methods use a manual physical method of circumscribing each colony with a needle or similar device within a culture plate with fairly large wells (for example, 1, 6, 12 well plates) that can be practically manipulated by hand. The circumscribed colonies are then broken into smaller sub colony pieces using a needle for distribution into new culture vessels for expansion of the population of stem cells. Other, less frequently employed methods use enzyme treatments (for example, trypsin, collagenase, etc.) to dissociate cells for subsequent transfer ('passage') into new culture vessels for expansion. The above methods to break up or section cell colonies typically suffer from (1) considerable time, (2) manual effort, (3) limited scalability, and (4) a wide size distribution of resulting colonies making it difficult to develop robust, routine, higher throughput methods of managing ES/iPS cell cultures. Also, it is currently difficult to use higher density multi-well plates, such as 96 W and 384 W, typically used in high throughput biology, due to their lack of suitability for these manual colony manipulations.

In some aspects, the technology described herein can provide improved, automated, high-throughput and scalable methods for passaging ES/iPS cells for propagation leading to colonies of more uniform size with greater viability and outgrowth. Additionally, the description permits the selection of individual colonies based on expression of phenotypic markers, such as surface markers, morphology, and molecularly expressed sensors or reporters. The method also permits use of a variety of multi-well plates typically used in high throughput biology applications.

The ability to consistently achieve more uniform sizes of cell sub colonies permits production of more robust ES/iPS cell cultures for screening compounds and agents that maintain pluripotency, and improved efficiency of subsequent differentiation and maintenance of the differentiated state. Larger numbers of smaller colonies can be placed into multi-well plates providing greater coverage of the culture surface. Upon outgrowth, additional coverage can be attained. Such coverage can be an important aspect of permitting screening applications. Sometimes, ES/iPS cells begin to differentiate on one or more edges of a cell colony before the rest of the colony becomes differentiated and thus, are not useful as ES/iPS cells. Thus, embodiments of the present disclosure also provide methods for separating the usable ES/iPS from the differentiated cells.

In some aspects, the technology described herein additionally offers surprisingly and unexpectedly improved, automated, high-throughput and scalable methods for sectioning confluent ES/iPS cell cultures for direct generation of embryoid bodies leading to uniform embryoid bodies of specific size with greater potential and efficiency of differentiation into specifically desired mature cell types. The ability to consistently generate uniform embryoid bodies of specific size permits more robust production of differentiated cells with specialized function. Larger numbers of uniform embryoid bodies of preferred size can be placed into stirred suspension bioreactors providing large scale production of mature cell types. Such production capability can be an important aspect of generating cells for clinical applications.

Throughout the present disclosure, ES/iPS cells are used as examples of cells that form colonies that may require separation for continued growth, purification, or differentiation. It will be appreciated by one of skill in the art in view of the present disclosure, however, that the methods disclosed herein may be applied to any type of cells that form colonies and/or that would benefit from sectioning or subculturing, for example.

In some embodiments, methods of the present disclosure (and devices for performing methods of the present disclosure) can involve sectioning living cell colonies using electromagnetic radiation, for example, from lasers. For example, one method of sectioning cell colonies includes providing a cell colony on a culture surface that has a known thickness; locating the position of the bottom of the culture plate using automated focus technology; defining an offset of focal position from the bottom of the culture plate to an optimal position for laser sectioning; and sectioning a portion or all of the entire culture into one or more pieces using a pattern of laser cutting lines.

In some embodiments, another method of sectioning cell colonies can include, for example, providing a cell colony on a surface; imaging the cell colony in a culture; selecting one or more colonies of specific phenotype for sectioning; and sectioning the selected cell colony(ies) into one or more pieces using the pattern of laser cutting lines. Another method of sectioning cell colonies includes, for example, providing a cell colony on a surface; imaging the cell colony; selecting a phenotype for sectioning; and sectioning the selected cell colony into one or more pieces using a pattern of laser cutting lines. Another method of sectioning cell colonies includes, for example, providing a cell colony on a surface; imaging the cell colony; selecting one or more colonies of specific phenotype for sectioning; identifying an edge of the selected colony(ies); providing a sequence of laser pulses around the cell colony to separate the cell colony from the rest of the culture; and sectioning the cell colony into one or more pieces using a pattern of laser cutting lines.

Several non-limiting examples of embodiments are discussed below. In some aspects, each can vary in terms of providing complexity and permitting varying levels of scalability and selectivity.

A first non-limiting embodiment includes providing a living cell colony; imaging the cell colony; selecting a colony with specific phenotype for sectioning; identifying at least part of an edge of the colony; providing a sequence of laser pulses around the identified edge of cell colony to separate the cell colony from the rest of the culture; and sectioning the cell colony into one or more pieces using a pattern of laser cutting lines.

In some embodiments, the cultures of living cells, for example, ES/iPS cells may be imaged in either transmitted light (for example, brightfield (BF), phase contrast, darkfield, differential interference contrast) and/or fluorescence, for example. As illustrated in FIG. 1, living iPS cell colonies may exhibit a distinct textural contrast or fluorescence intensity from feeder cells or extracellular matrix.

Figure 2:
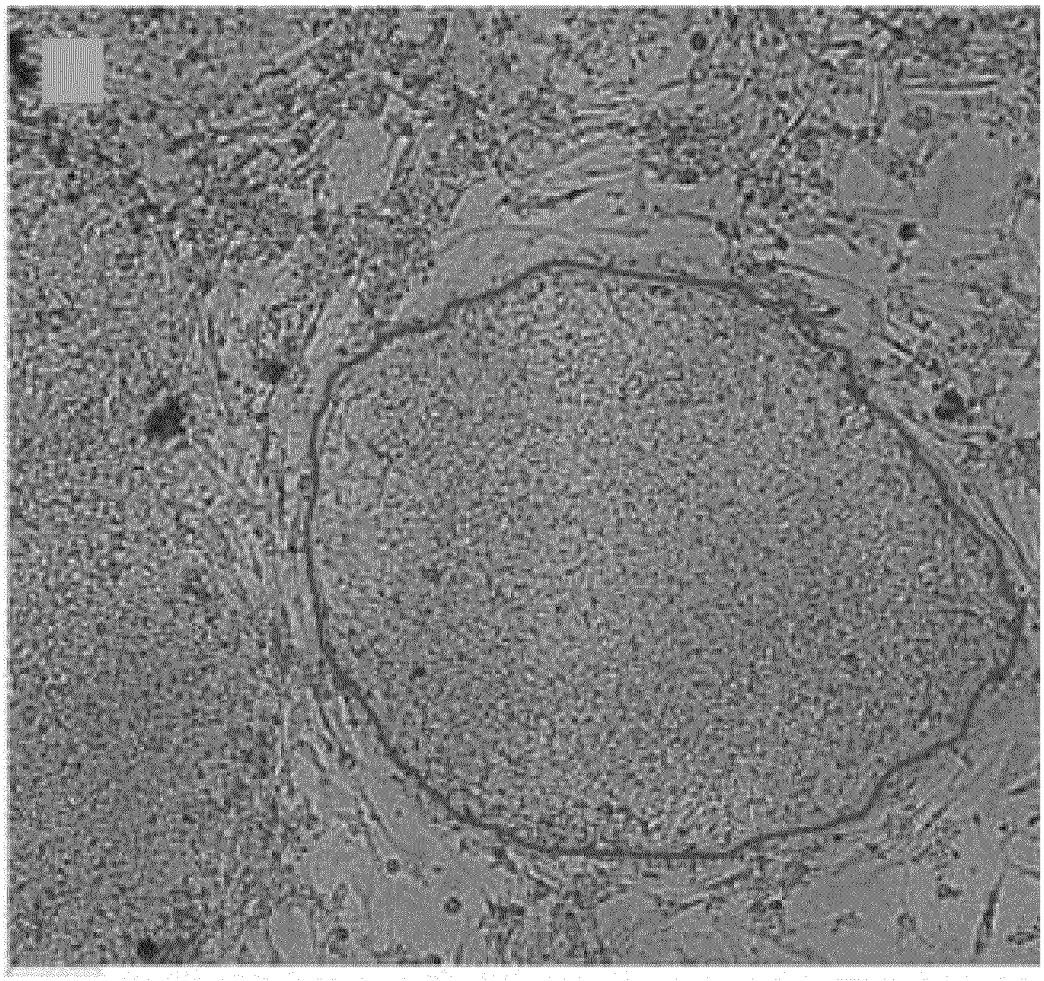
FIG. 2 illustrates an image with an edge of an iPS cell colony identified by image analysis prior to sectioning of the cell colony.

As illustrated in FIG. 2, the image may be segmented prior to sectioning to identify one or more stem cell colonies with a selected phenotype. 'Segmentation' is a term understood by one of skill in the art to include image analysis process for separating objects within an image.

Figure 3:
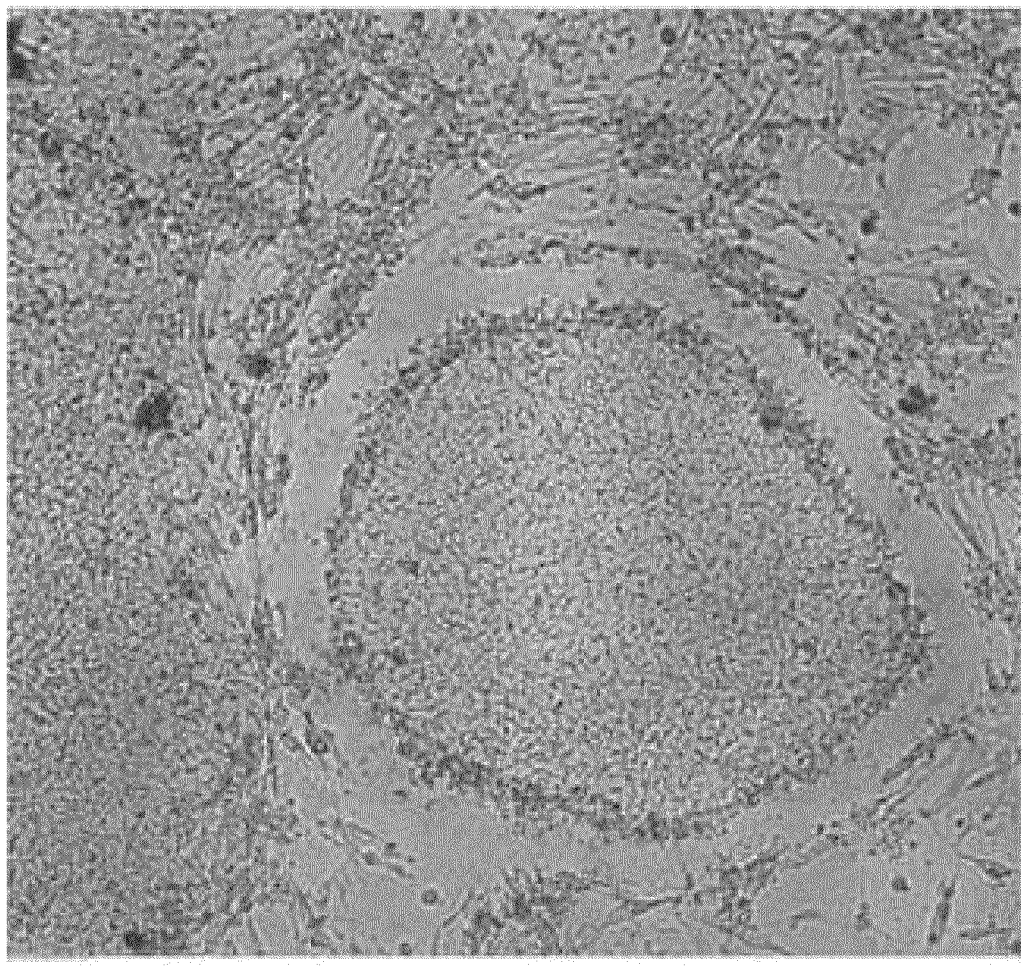
FIG. 3 illustrates an iPS cell colony after a sequence of laser pulses were delivered around the edge of the colony, thus separating the colony from the rest of the culture.

As illustrated in FIG. 3, the coordinates from the segmentation process can be used to identify the edge of the colony and can be used to position a sequence of laser pulses of an optimal size and power (laser cutting lines) around the colony, separating the colony from the rest of the culture using any suitable device, including for example, the LEAP™ Cell Processing Workstation (Cyntellect Inc., San Diego, Calif.).

Figure 4:
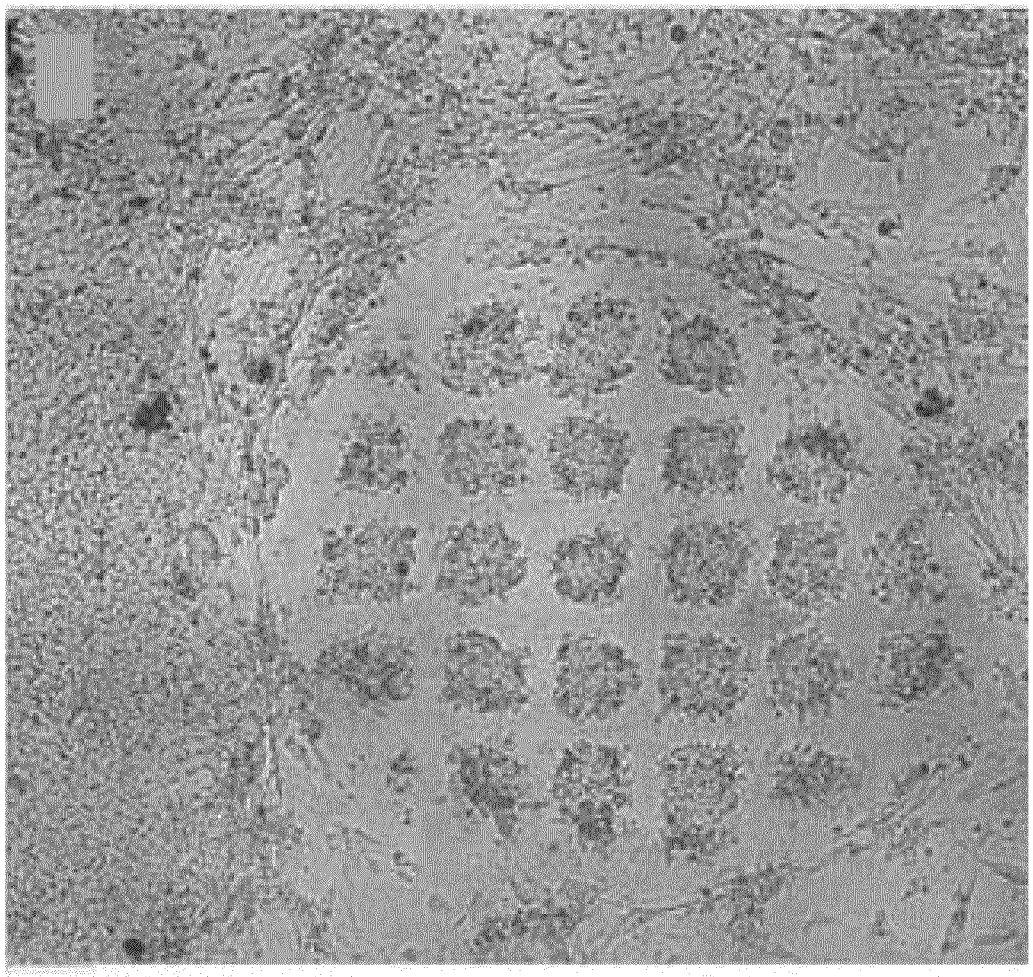
FIG. 4 illustrates a separated iPS cell colony sectioned into a number of relatively uniform sub colony pieces using a grid pattern of laser cutting lines.

As illustrated in FIG. 4, the isolated colony then can be sectioned into a number of relatively uniform pieces using a grid of laser cutting lines. The size of the pieces can be controlled by changing the distance between the laser cutting lines. The shape of the pieces can be controlled by independently changing the distance between the horizontal vs. vertical laser cutting lines. The shapes of the pieces can be arbitrary and controlled by defining the pattern of the laser cutting lines.

Figure 5:
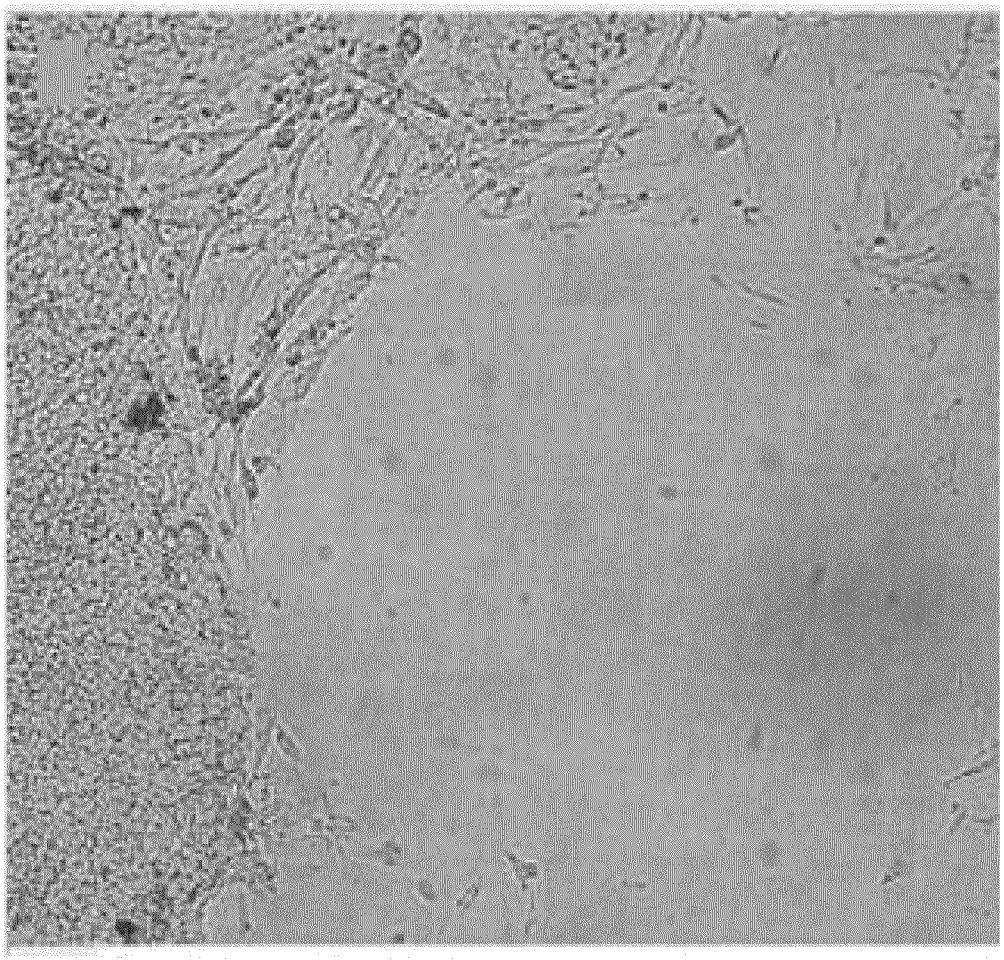
FIG. 5 illustrates feeder cell areas still intact after removal of sub colony pieces.
Figure 6:
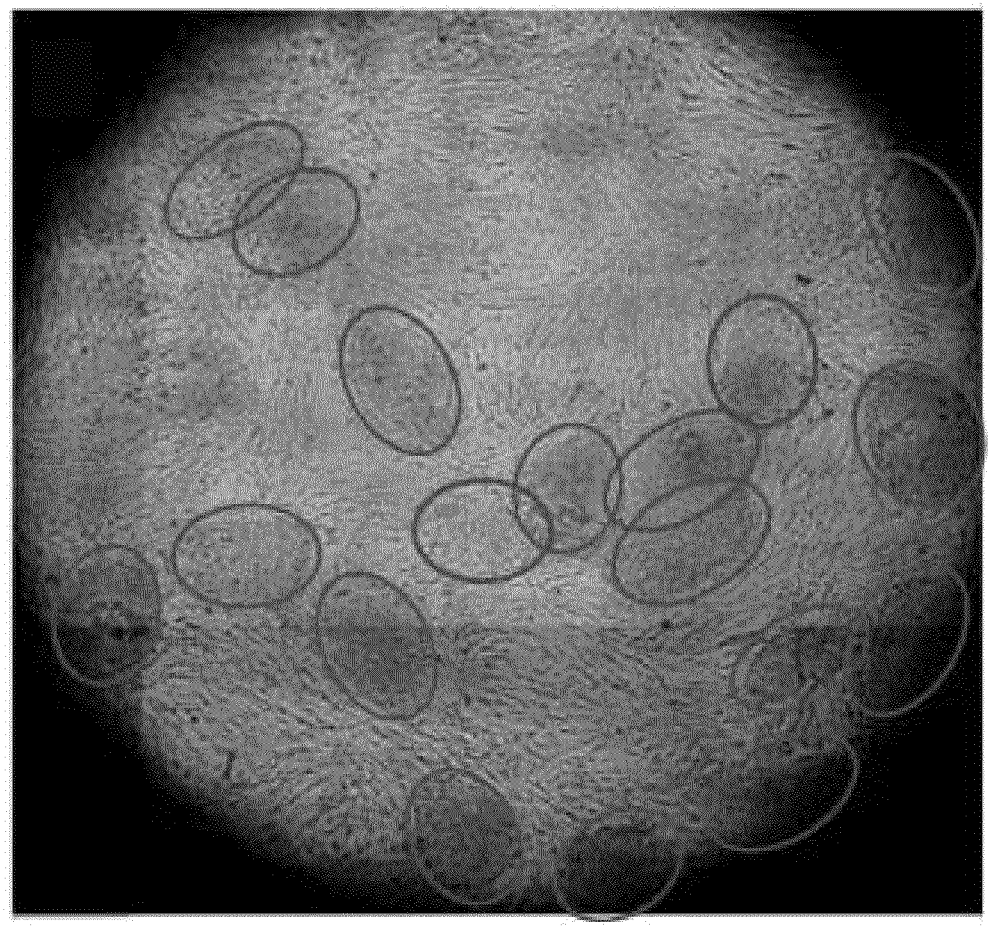
FIG. 6 illustrates resulting iPS cell sub colonies using methods of the present disclosure, which are generally more uniform than manually or enzymatically passaged ES/iPS cell colonies.
Figure 11:
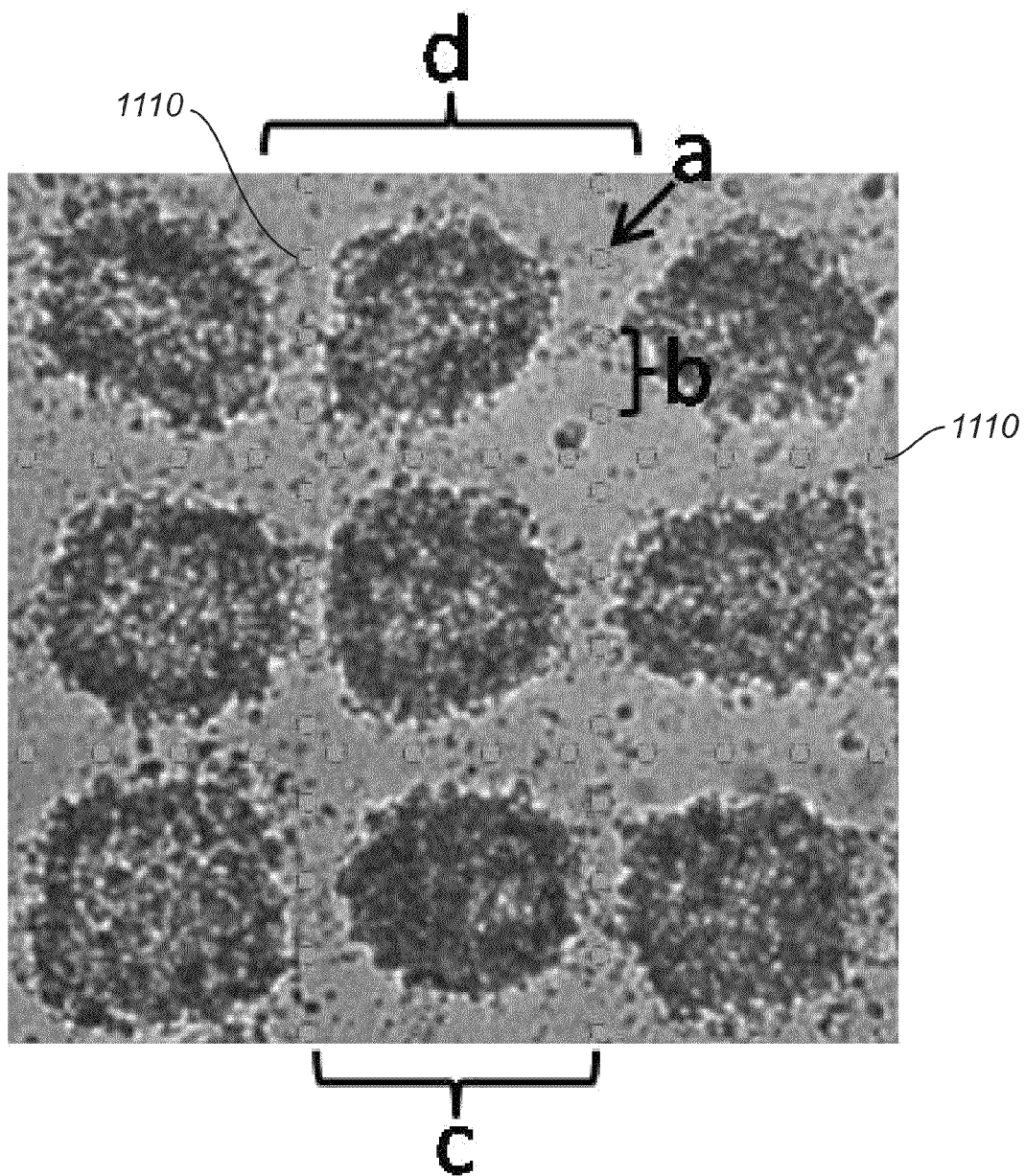
FIG. 11 diagrams the pattern of laser cutting lines positioned across an iPS cell cultures. Figure part (a) shows one laser pulse along the laser cutting line 1110, which may be shot using a range of laser energies from 1-50 µJ per pulse, laser spot size radii from 1-20 µm, and 1-5 laser pulses and/or repeats. Figure part (b) is the distance between laser pulses along the laser cutting lines 1110, which is typically 16 µm, but may range from 5-50 µm. Figure part (c) is the distance between two laser cutting lines 1110, which may range from 20-2000 µm. Varying the distance between laser cutting lines 1110 allows for sectioning of cultures in various sizes and shapes. Optimal section sizes for enzyme-free removal of sub colonies is 20-300 µm. Optimal section sizes for use in differentiation of stem cells into mature specialized cells is 250-2000 µm. Figure part (d) is the actual width of the sectioning lines in the culture which are wider than the diagramed laser cutting lines due to the laser action loosing the edges of the cell sections.

The pieces of the sectioned colony may then be removed from the well by any suitable technique, including for example, any suitable fluid pipetting techniques with or without the addition of additional chemicals, such as enzymes, to facilitate the release of the pieces. Some embodiments do not require additional chemicals. The pieces of the colony can be less adherent to the culture bottom after cutting due to the laser action loosening the cell sub colonies, permitting use of fluid pressure from a pipetting device (manual or motorized) to dislodge the pieces into suspension within the fluid of the culture vessel (FIG. 11). No laser catapulting is required to dislodge sub colony pieces. Upon suspension, the pieces are transferred via fluid removal to a new culture vessel prepared to receive the pieces for subsequent culture. After removal of sub colony pieces, cultures often have most of the non-colony areas still intact, whereas the areas previously occupied by colonies are relatively clear. FIG. 5 illustrates non-colony areas still intact after removal of sub colony pieces whereas colony areas have been cleared out. As illustrated in FIG. 6, the pieces, and colonies, which develop from them upon subculture, and which result from this method are generally more uniform than manually or enzymatically passaged ES/iPS cell colonies. Since any feeder cells are typically unable to proliferate, the transfer of any feeder cells will simply be debris that can be washed out of the new culture.

The laser-mediated mechanism for sectioning the colonies can be any that is suitable, including for example, one such as photothermal, photomechanical, or photochemical. A preferred embodiment is the use of the selective photothermal killing of cells at the focal point of the laser. This approach usually includes the addition of a dye that absorbs the laser wavelength causing an increase in temperature, effectively photocoagulating the cells in place. The photomechanical approach does not require additions to the culture and generally involves physical destruction of the cells at the focal point of the laser. In some aspects this approach can utilize significantly more laser power and may cause some collateral damage in the culture. The photochemical approach involves use of a UV laser that induces selective apoptosis at the focal plane of the laser. This approach can require more time, for example, 2-3 days before cells die leading to effective sectioning.

Figure 7:
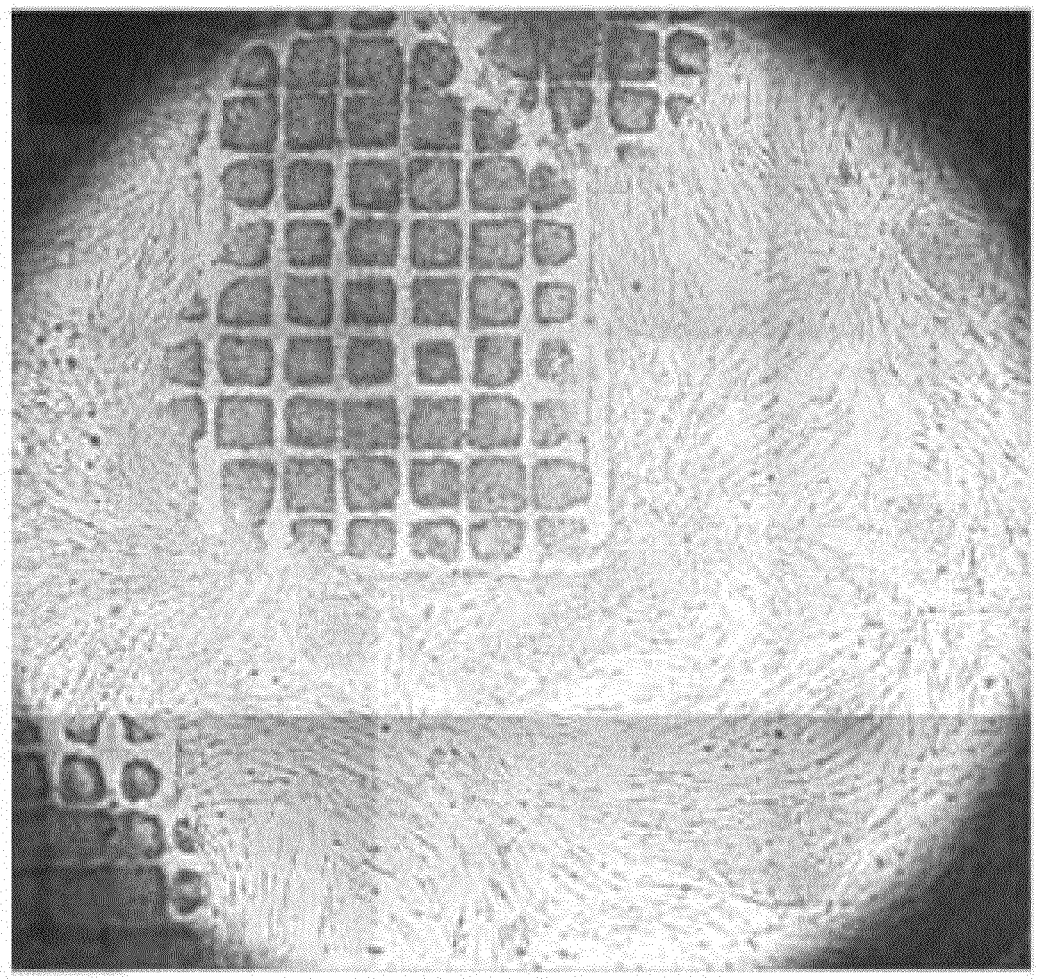
FIG. 7 illustrates laser cutting lines positioned across selected colonies without regard to the edges of the colonies.
Figure 8:
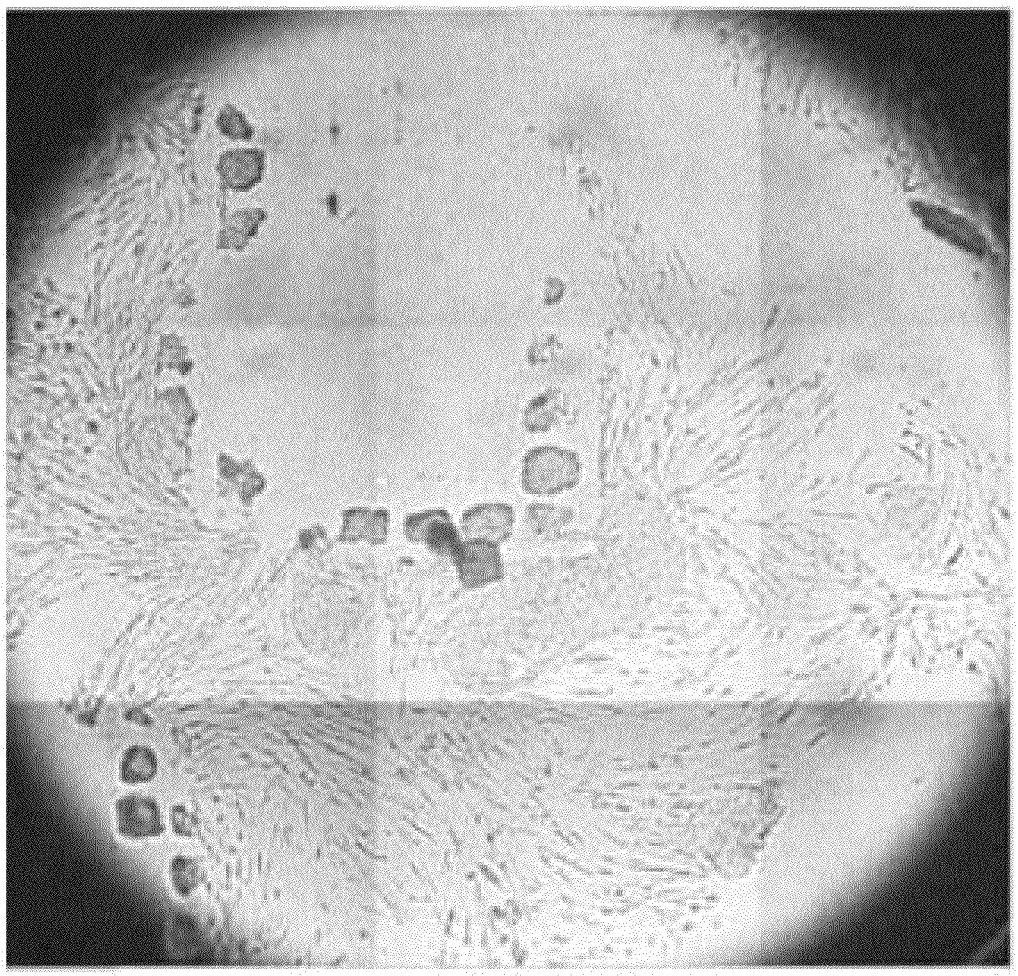
FIG. 8 illustrates a small fraction of sub colony pieces left behind after fluid pressure dispersion from cultures that had been sectioned without regard to the edges of the colonies.

A second embodiment is similar to the first, except laser cutting lines are positioned across selected colonies without specifically cutting along the edges of the colony. FIG. 7 illustrates laser cutting lines positioned across selected colonies without regard to the edges of the colonies. The limits of the laser cutting lines are restricted to within the identified boundaries of the colonies, leading to a similar effect but of higher throughput since the amount of laser cutting is reduced (no edge cut). As illustrated in FIG. 8, this approach has the potential of leaving behind some of the colony pieces after fluid pressure dispersion. This lower efficiency can be tolerated in certain high-throughput applications. The quantity of cells, for example, ES/iPS cells, left behind will be related to the size of the pieces cut.

Figure 9:
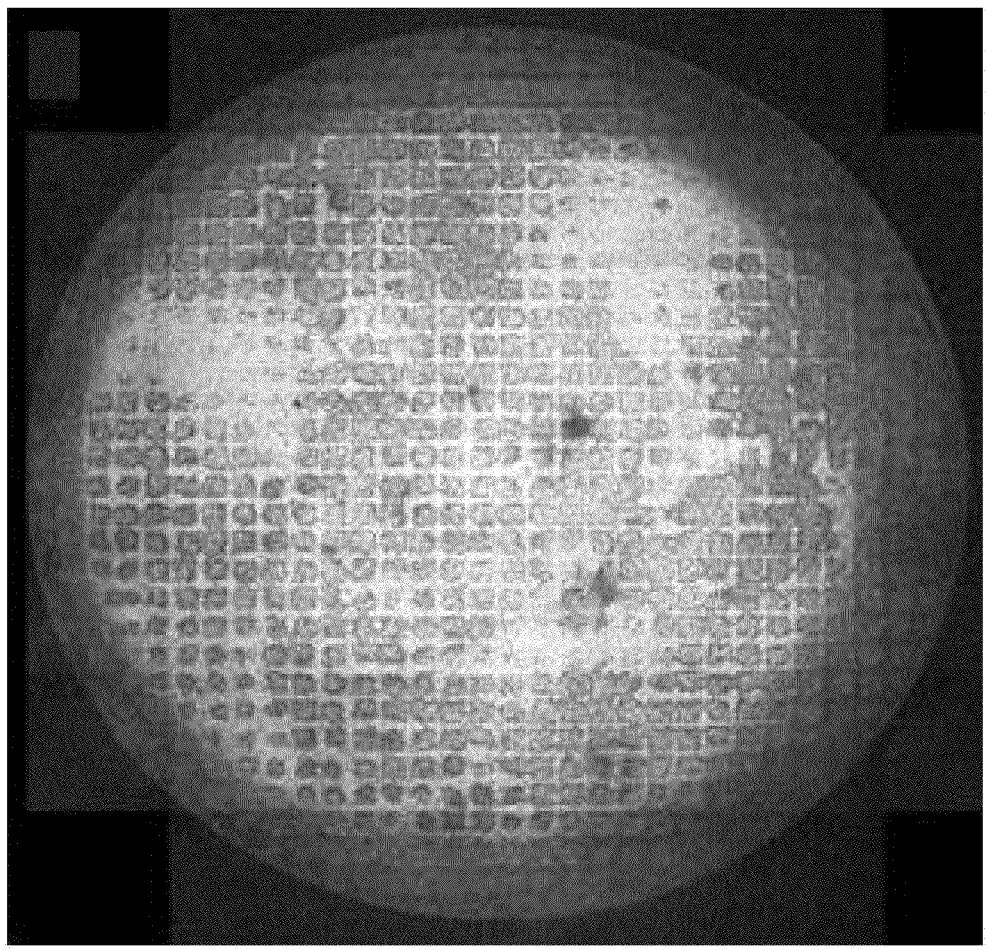
FIG. 9 illustrates an entire iPS cell culture sectioned with laser cutting lines without specifically identifying cell colonies and without regard to the edges of any colonies.
Figure 10:
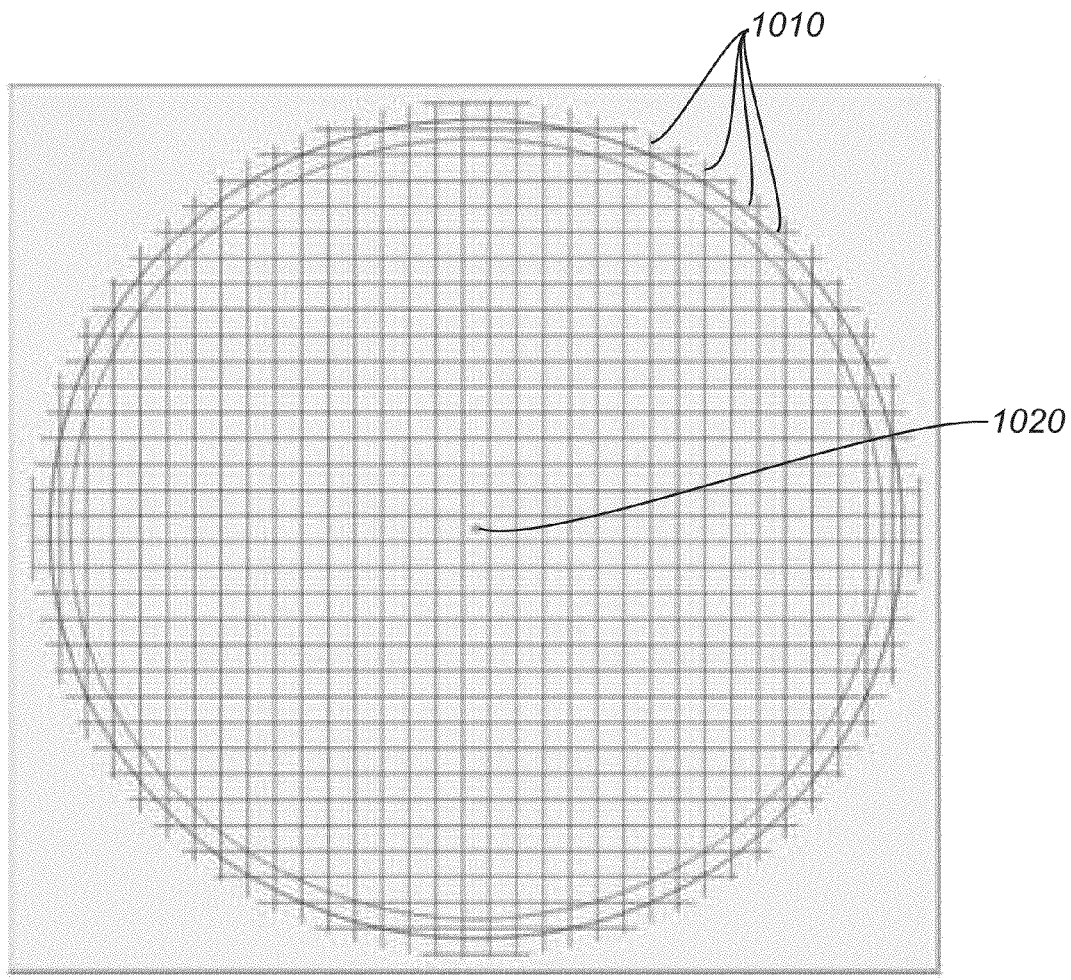
FIG. 10 diagrams the pattern of laser cutting lines positioned across the entire well used to section the iPS cell culture shown in FIG. 9. The laser cutting lines 1010 are positioned to cut 200 µm sections. Typical section sizes for iPS and ES cell sub colonies range from 20-400 µm. Dot 1020 indicates the position within the well where auto focusing and laser focusing will be performed.

A third embodiment involves a further simplification by placing laser cutting lines across the entire culture surface without segmenting the image of the colonies as illustrated in FIGS. 9 and 10. Thus, in some aspects the methods can be performed without having to identify a phenotype or cells displaying a phenotype prior to sectioning. This approach also will create pieces of any feeder layer which may be transferred to the new culture, but should not be a complication since feeder cells are proliferation incompetent and thus will die and be washed out of the new culture anyway. This approach is particularly high-throughput, requiring only the ability to focus on the culture, fire a pattern of laser cutting lines, fluidic suspension of the sub colony pieces and transferring them to new culture vessels. After attachment, debris derived from dead cells and transferred pieces of the feeder layer can be washed out. This third embodiment: (1) removes the need for specific image analysis of the colonies, significantly reducing the computational requirements; (2) requires fewer steps; and (3) allows a simpler apparatus to perform the operation.

A fourth non-limiting, embodiment is similar to the third, except laser cutting lines are positioned across the entire surface of colonies that have grown into a monolayer of cells. Although stem cells are not typically grown to confluence, the use of a monolayer of stem cells for this approach maximizes the efficiency of creating homogeneous pieces of cells, whereas use of a non-confluent culture decreases efficiency, thereby resulting in more heterogeneous pieces of cells. This approach creates uniform pieces of cells which are transferred to a culture vessel for the purpose of rapid expansion and/or production of differentiated cells with specialized function as shown in FIGS. 15 and 16. Large sub colony pieces may require addition of enzymes to facilitate the release of the pieces.

A fifth embodiment further simplifies the process by not requiring imaging of the culture. Once the optimal laser power, spot size, and Z-axis position is known for sectioning colonies, it is possible to automatically place the stem cell culture at the predetermined optimal position based on knowledge of the culture plate thickness and ability to find the position of the bottom of the culture plate using automated focus technologies. This position should be consistent for all plates of the same specification. This approach allows a much simpler apparatus, in that a camera and image processing and analysis are not required. Effective real-time autofocus mechanisms combined with higher pulse frequency lasers and large field optics can maximize throughput of production of uniform size stem cell colonies.

All embodiments may provide more rapid throughput and result in more uniform stem cell colonies than currently available techniques. Some of the embodiments provide selection of specific colonies based on colony phenotype(s) which may include colony or cell morphology, colony or cell size, colony or cell shape, colony or cell compactness, and fluorescence intensity of colonies or cells labeled with stem cell-associated markers. Selection of specific colonies (FIG. 2) may be made by visual inspection or by automated image analysis.

In some aspects, laser cutting lines may be created using the photomechanical approach in which no additives are required; photochemical in which apoptosis is induced using appropriate laser wavelengths (for example, 355 nm); or photothermal in which a laser light absorbing dye is added to the culture permitting significant temperature increases at the position of the laser spot photocoagulating cells. Photomechanical approaches can lead to wider laser cutting lines potentially eliminating more desirable cells. A benefit of photothermal is the reduced laser power required leading to smaller areas of cutting, preserving more cells and increasing yields. No ill effects of using an absorptive dye, such as Allura Red, have been observed when ES and iPS cells have been cultured in the presence of the dye.

Optionally, the fluidic pressure used to dislodge and stir the sub colony pieces can be substituted with shear forces created by the generation of cavitation bubbles or thermal gradients using the laser, thereby decreasing the complexity of the pipetting mechanism and reducing the procedure to simple transfer of the sample to the next culture vessel.

The methods disclosed herein provide numerous advantages, including many unexpected and surprising advantages. Some of those advantages may include, for example, increased scale of culturing, enabling new and unique experimentation, data rate, interoperability or lower cost. In some embodiments, advantages include automated sectioning of stem cells such as ES/iPS cells. In some embodiments, advantages include increased scalability of stem cells, including for example, ES/iPS cell cultures. In some embodiments, advantages include high-throughput production of more uniform stem cell colonies, including for example, ES/iPS cell colonies. In some embodiments, advantages include lower cost to maintain stem cells, for example, ES/iPS. In some embodiments, advantages include reduced personnel and training requirements. In some embodiments, advantages include permitting practical high-throughput biology with stem cells. Is some embodiments, advantages may include providing more efficient, controlled and uniform differentiation. As noted above, ES/iPS cells are used as examples of cells that form colonies that may require separation for continued growth or purification. It will be appreciated by one of skill in the art informed by the instant disclosure that the methods disclosed herein may be applied to any type of cells that form colonies and that the described advantages can apply to other types of stem cells and non stem cell colonies. Colonies can be made of any cell type that forms a collection of cells in a colony, such as non-ES/iPS cells, tumor spheroids, neurospheres, embryoid bodies, embryonic germ cells, embryonic carcinoma cells breast cancer stem cells, and cancer stem cells.

EXAMPLES

Example 1

Generation of iPS Cell Cultures With More Uniform Colony Size

Figure 12:
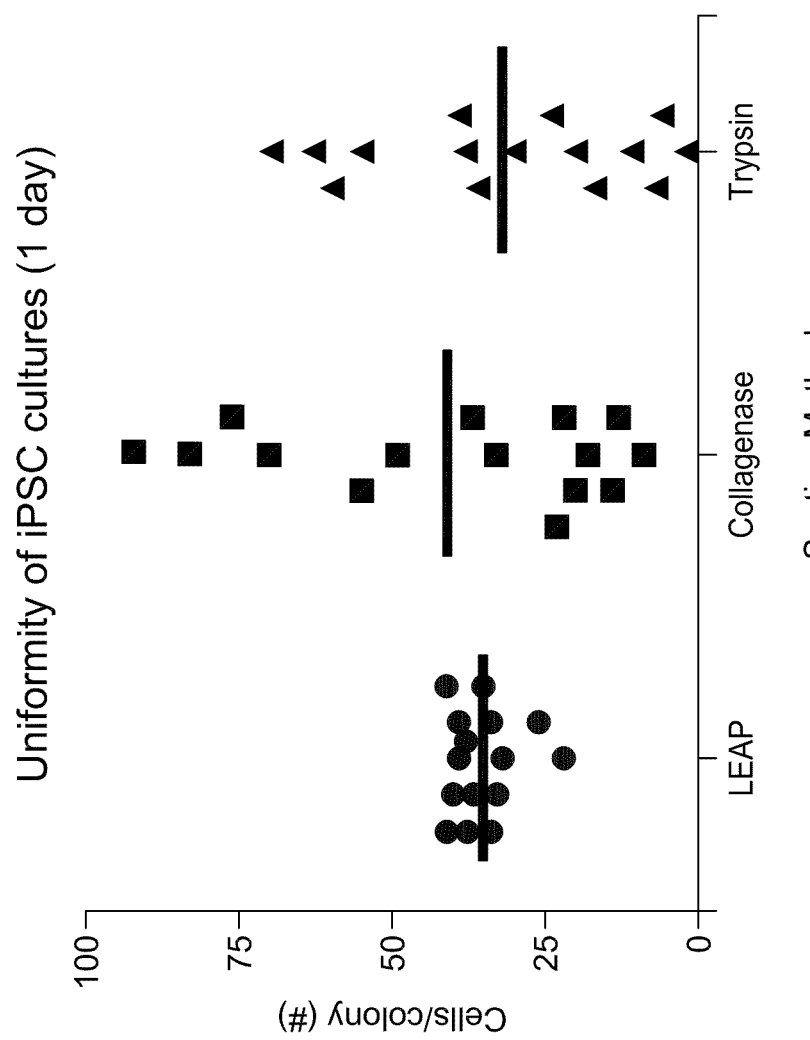
FIG. 12 illustrates the more uniform size distribution of sub colony pieces derived from uniform sectioning of colonies by the current technology as compared to typical enzymatic methods (collagenase and trypsin).
Figure 13:
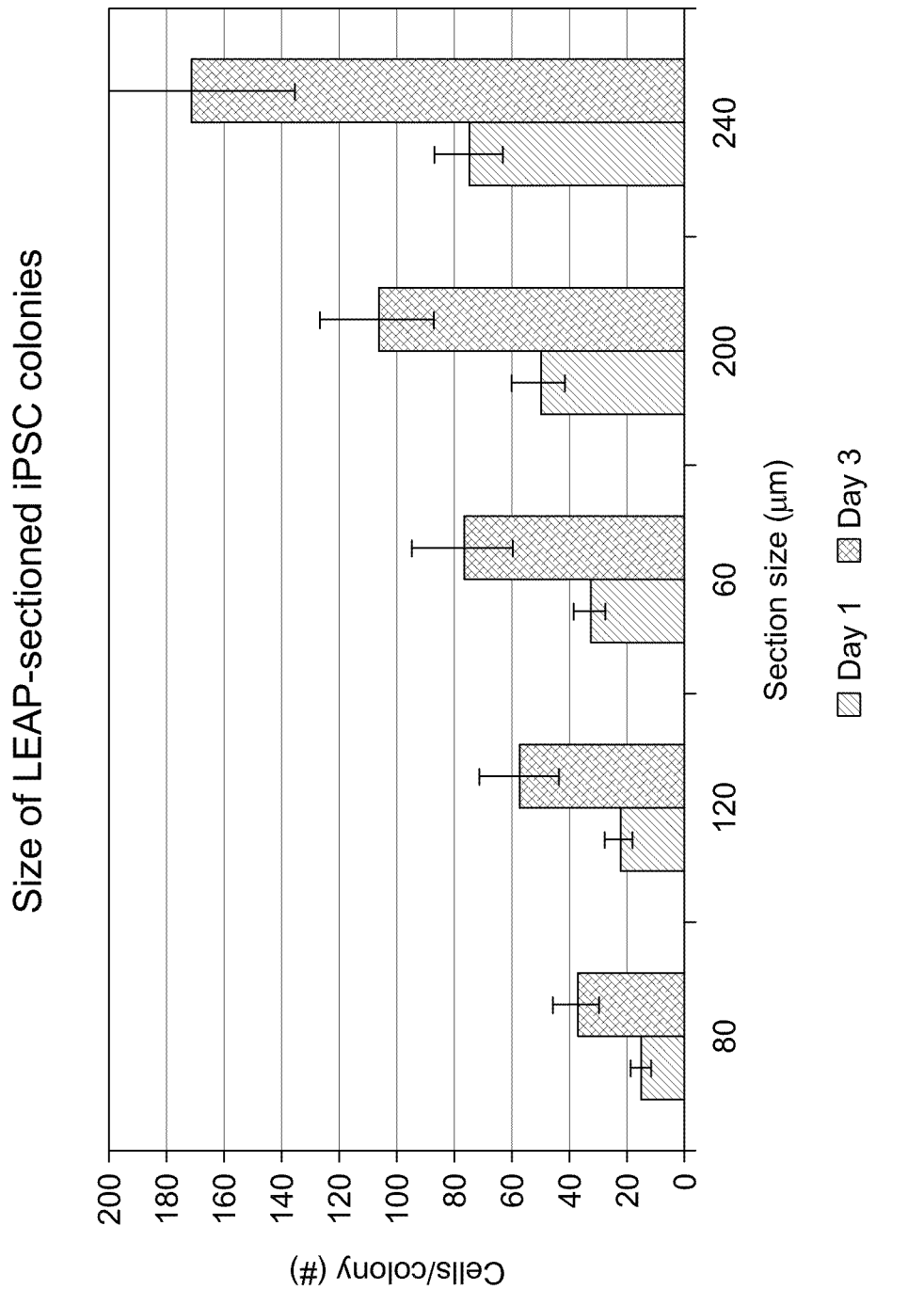
FIG. 13 illustrates the relationship between the size of the square sections that are cut and the resulting sizes of the transferred sub colonies after 1 day and 3 days of culture.
Figure 14B:
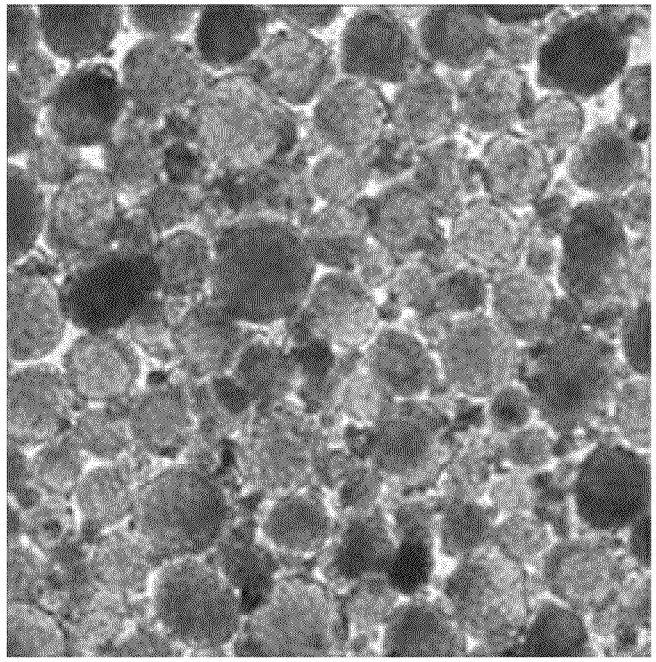
FIGS. 14A, 14B, and 14C illustrate the more uniformly sized embryoid bodies formed from colonies sectioned by the current technology as compared with embryoid bodies sectioned by collagenase treatment
Figure 14A:
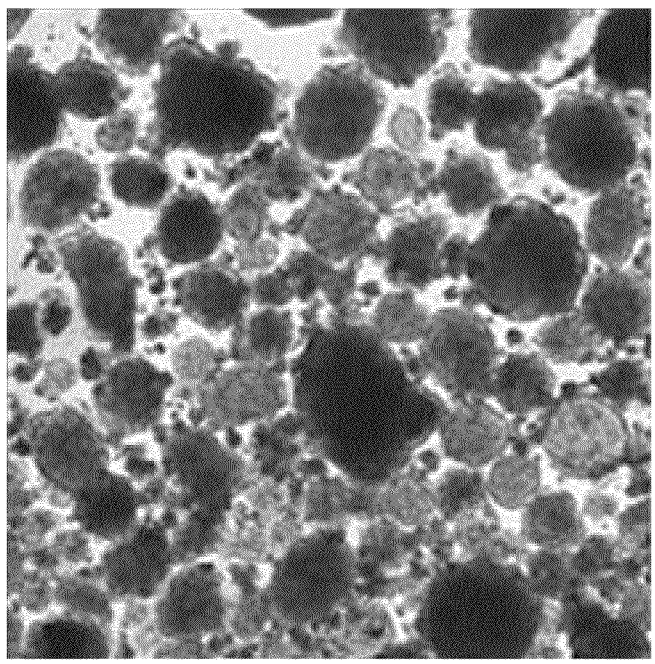
Figure 14C:
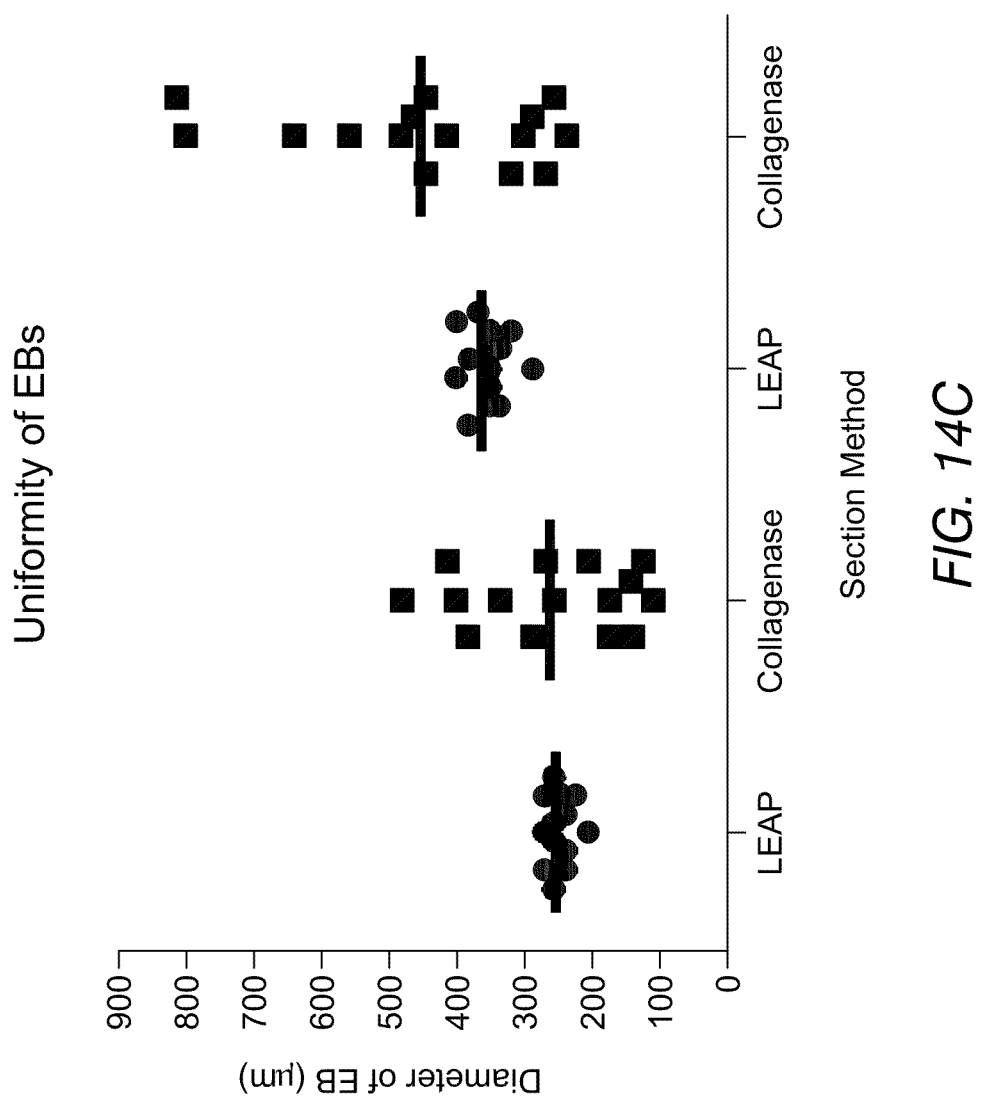

This experiment describes laser-mediated sectioning of human iPS cell colonies using the LEAP Workstation. Human iPS cells were sectioned by typical methodology (i.e., enzymatic sectioning using collagenase IV (Invitrogen) onto 96-well plates (Corning)). Cultures were incubated in a cell culture incubator at 37° C. in complete stem cell medium (Thomson J. A, et al. "Embryonic stem cell lines derived from human blastocysts" (1998) Science; 282:1145-1147; which is incorporated herein by reference in its entirety)] for five days. On the fifth day, cultures were washed once with PBS (Invitrogen) and fresh stem cell medium containing 4 mg/ml Allura red (Sigma) was added to the tissue culture wells for laser-mediated photothermal processing. Cultures were imaged using brightfield imaging on LEAP (FIG. 1) and human iPS cell colonies were identified by morphology and segmented using LEAP stem cell manager software (FIG. 2). Colonies of a specific size were then selected for laser-mediated sectioning. Once the population of colonies to be sectioned was selected, the edge of each colony was targeted using a series of 532 nm laser pulses at approximately 1 kHz, with an energy of 3.25 µJ per pulse and a laser spot radius of 6 µm on LEAP. Two repeats of one laser pulse were used to process a series of spots in a line around the edge of each colony (FIG. 3). Next, each colony was sectioned into 160 µm squares using a series of 532 nm laser cutting lines at an energy of 3.25 µJ per pulse and a laser spot radius of 6 µm with a pulse spacing of 16 µm. Again, two repeats of one laser pulse were used to section the colonies into pieces (FIG. 4, 6, 9, 11). Cultures can be processed using a range of laser energies from 1-50 µJ per pulse, laser spot size radii of 1-20 µm, pulse spacing of 5-50 µm, using 1-5 repeats per spot. Suitable sub colony size was determined by sectioning colonies into several sizes ranging from 20-400 µm (FIG. 13). Sub colony pieces were removed by manually pipetting, leaving behind any cells that were not isolated nor sectioned (FIG. 5). Cells propagated using this method were monitored over five days and retained a morphology characteristic of iPS cells. Colonies generated using this method were more uniform than typical enzymatic sectioning of iPS cell cultures (FIG. 6). Cultures sectioned using laser or enzymatic methods (collagenase, trypsin) were stained with Hoechst one day after passage and the number of cells per colony were manually counted (FIG. 12, LEAP) to demonstrate the improved uniformity of laser-sectioned cultures as compared with enzymatic methods. After 5 days, cultures sectioned using laser or collagenase were subjected to in vitro differentiation analysis by embryoid body formation. Embryoid bodies were monitored over 8 days in suspension culture and the diameter of each embryoid body was measured. Embryoid bodies generated from laser sectioned iPS cell cultures were more uniform in size that collagenase sectioned cultures (FIG. 14).

This example describes the rapid automated generation of populations of iPS cell colonies of more uniform sizes than obtained by currently used methods.

Example 2

Generation of Differentiated Cells With Specialized Function Using iPS Cell Pieces With Uniform Specific Size This experiment describes laser-mediated sectioning of human iPS cells into specific size pieces for the purpose of generating embryoid bodies (EBs) using the LEAP Workstation. Human iPS cells were sectioned at high density by typical methodology (i.e., enzymatic treatment using collagenase IV (Invitrogen) onto 96-well plates (Corning)). Cultures were incubated in a cell culture incubator at 37° C. in complete stem cell medium until a confluent monolayer of human iPS cell colonies was observed (5 days). On the fifth day, cultures were washed once with PBS (Invitrogen) and fresh stem cell medium containing 4 mg/ml Allura Red (Sigma) was added to the tissue culture wells for laser-mediated photothermal sectioning. Cultures were sectioned into specific size human iPS sub colony pieces by placing laser cutting lines across the entire surface without segmenting the image into discrete colonies. Cultures were sectioned into 250-2000 μm squares using a series of 532 nm laser cutting lines at an energy of 4.5 μJ per pulse, a laser spot radius of 5 μm, and a pulse spacing of 16 μm delivered at the optimal laser focal plane. Although not required, in this experiment the optimal laser focal plane was determined by a novel approach described below (FIG. 15,17).

This novel but not-limiting approach to identify the optimal laser focal plane can include the following steps: (1) optional automatic determination of the brightfield focus position, for example, by standard image analysis to determine the z-position with the greatest contrast image; (2) movement of the laser focus to 100 μm above the brightfield focus position (or an arbitrary position); (3) shooting of 5 laser shots, acquiring an image, and using image analysis, determining the amount of cell movement (i.e., to determine if the area shot by the laser has been cleared of cells); (4) Sequential shooting and analysis (as in step 3) in 10 μm z-step increments until the Z position exhibiting the most movement has been identified (this is the optimal laser focus position having the greatest effect on the cells being shot). The laser focus searched 200 μm total (100 μm above and below the brightfield focus or arbitrary position) in 10 μm increments.

Figure 18:
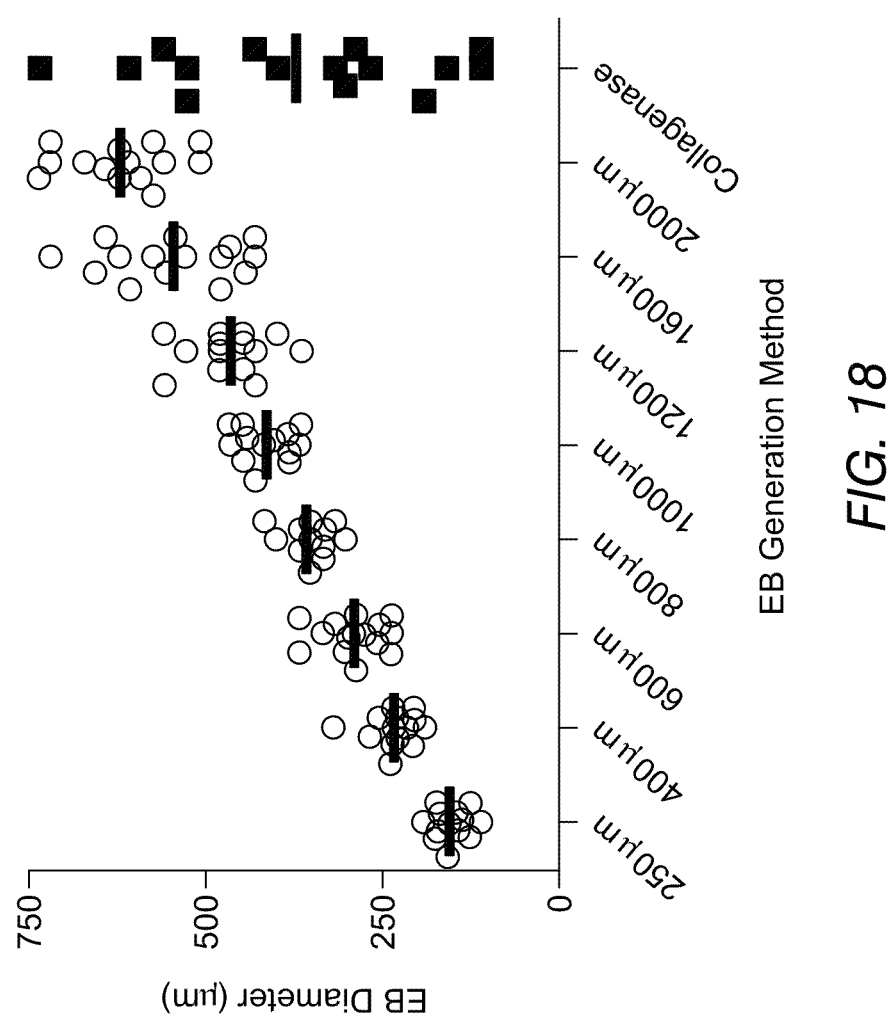
FIG. 18 illustrates the different three-dimensional embryoid body sizes consistently formed by varying the two-dimensional square section size used to section cultures by the present method as compared to variable collagenase sectioning.
Figure 19:
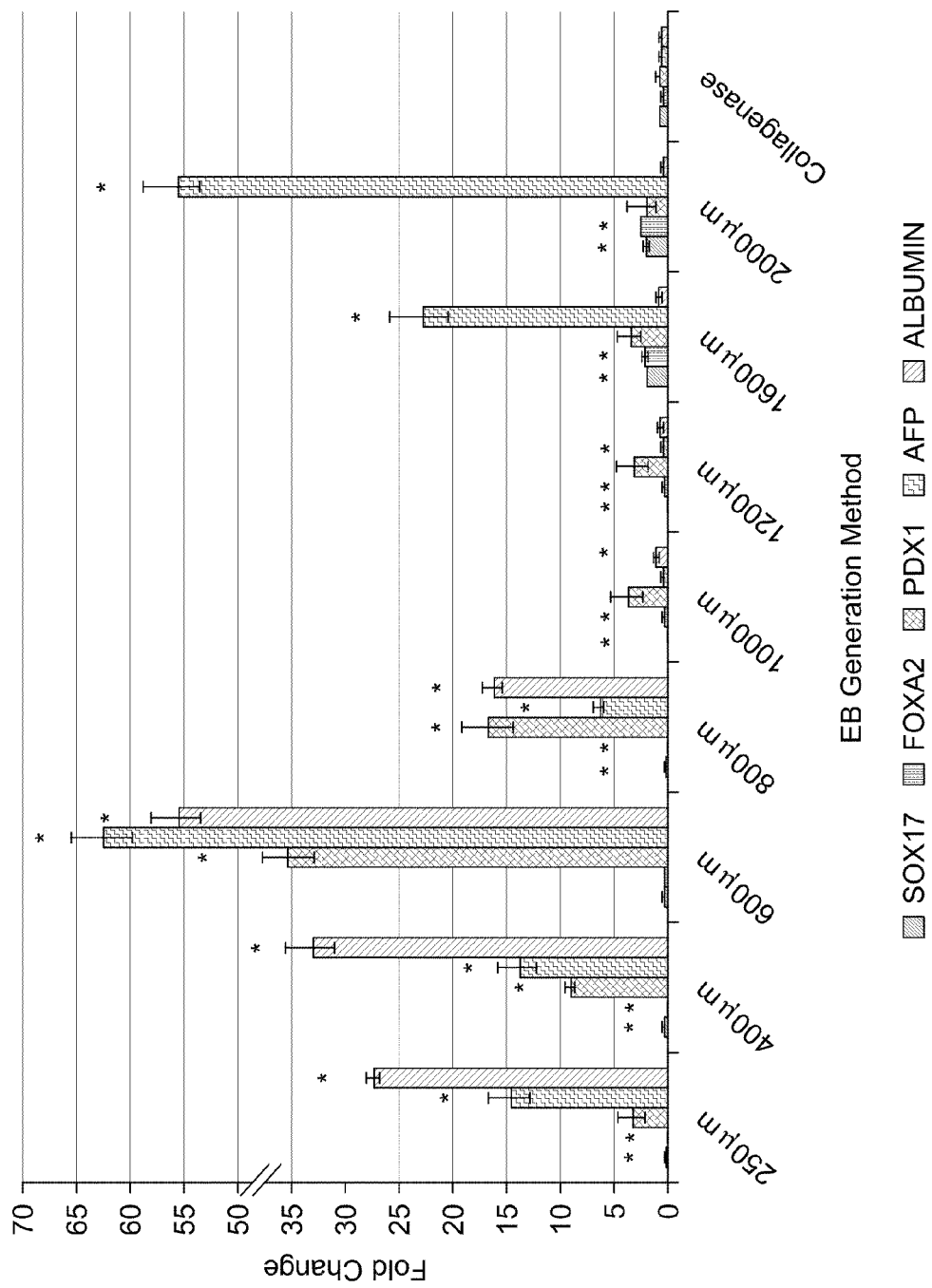
FIG. 19 illustrates the resulting differentiation potential of iPS cells into endodermal cells (as measured by RT-PCR expression of endodermal specific genes (Sox17, FoxA2, Pdx1, Afp, Albumin) 24 days after sectioning entire cultures as shown in FIGS. 15A, 15B, and 15C.
Figure 20:
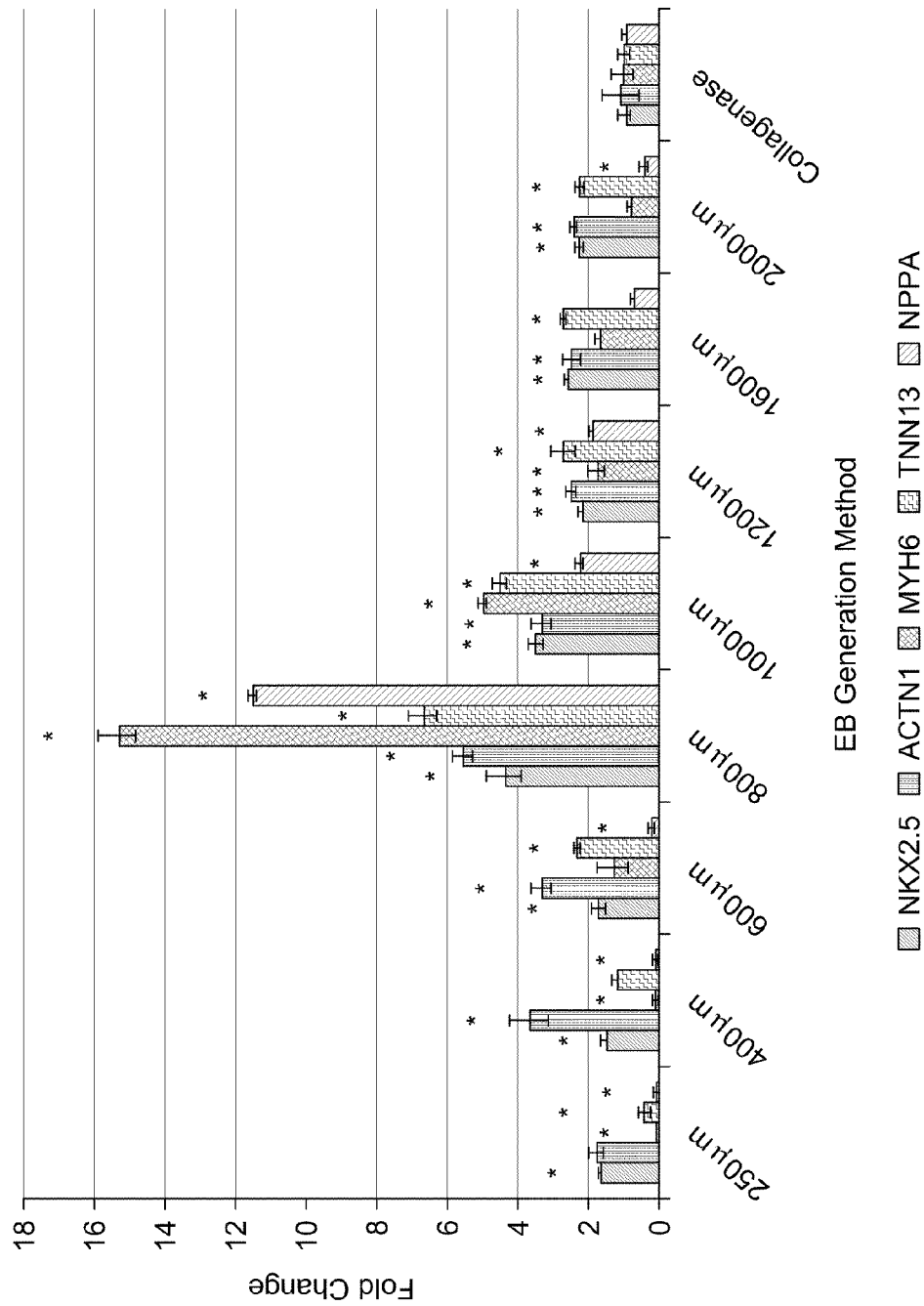
FIG. 20 illustrates the resulting differentiation potential of iPS cells into cardiomyocytes (as measured by RT-PCR expression of cardiomyocyte specific genes (Nkx2.5, Actn1, Myh6, TnnI3, NPPA) 22 days after sectioning entire cultures as shown in FIGS. 15A, 15B, and 15C.
Figure 21:
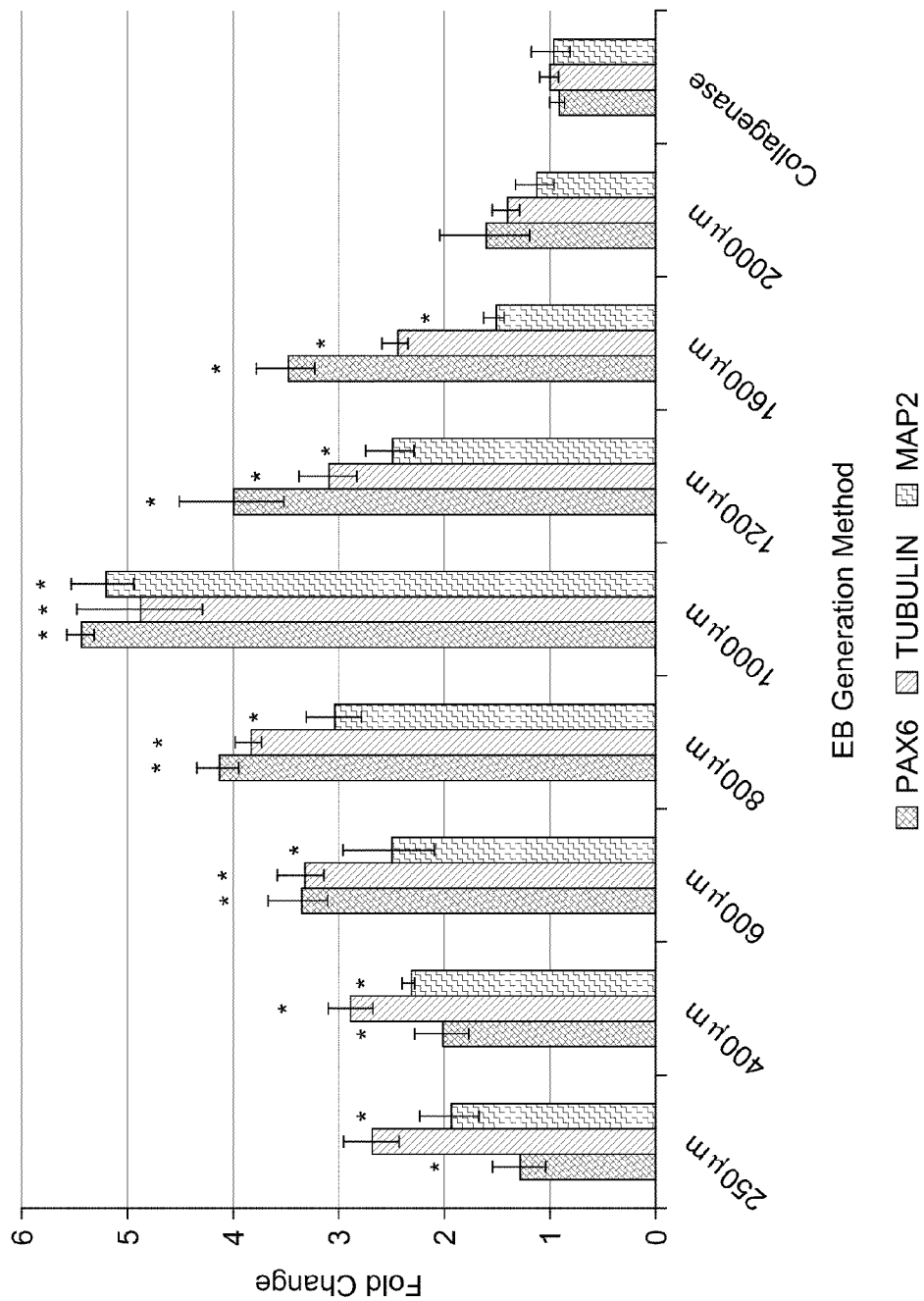
FIG. 21 illustrates the resulting differentiation potential of iPS cells into neurons (as measured by RT-PCR expression of neuron specific genes (Pax6, Tubulin3, Map2) 32 days after sectioning entire cultures as shown in FIGS. 15A, 15B, and 15C.

Fresh medium containing 1 mg/ml of collagenase IV was added to sectioned wells and after 1 hour, human iPS sub colony pieces were removed by manually pipetting. Human iPS sub colony pieces were transferred to low attachment plates (Corning) in complete stem cell differentiation medium. Four days after transfer to suspension culture, human iPS sub colony pieces formed well-defined uniform EBs of varying size (FIG. 16). Images were acquired of EB cultures generated using laser and typical methodology (collagenase), and the diameter of each EB was measured to demonstrate the uniformity of EBs generated by laser-sectioning. LEAP was used to control the size of resulting EBs by varying the size of human iPS sub colony pieces used to form EBs (FIG. 18). EBs generated using laser-sectioning were more uniform than typical EB generation methods (collagenase, FIG. 18). EB cultures generated using human iPS sub colony pieces ranging from 250-2000 μm square were induced to differentiate into mature cell types of all three germ layers to demonstrate the improved differentiation potential of EBs of specific size. After 24 days, quantitative real time PCR (QRT-PCR) analysis showed that EBs generated using 600 μm hiPSC pieces differentiated more efficiently into endoderm (hepatocyte-like) cells (FIG. 19). After 22 days, QRT-PCR analysis of mesoderm differentiation showed that EBs generated using 800 μm pieces differentiated more efficiently into cardiomyocytes (FIG. 20). After 32 days, QRT-PCR analysis of ectoderm differentiation showed that EBs generated using 1000 μm pieces differentiated more efficiently into neurons (FIG. 21). Thus, the yield and purity of specific types of differentiated cell progeny from iPS/ES cells can be increased by controlling the size of cell sections that are used for EB formation.

This example describes the increased efficiency of production of differentiated cells with specialized function using uniform EB populations of specific size. The method used to control the size of the formed EBs is highly reproducible and automated, making it very useful for generating certain cell types from ES/iPS cells. Further, specific size ranges of sections and resulting EBs were identified that contribute to the increased differentiation potential of endoderm, mesoderm, and ectoderm.

Example 3

Isolation of ES Cell Colonies for Generating New ES Lines

Figure 17B:
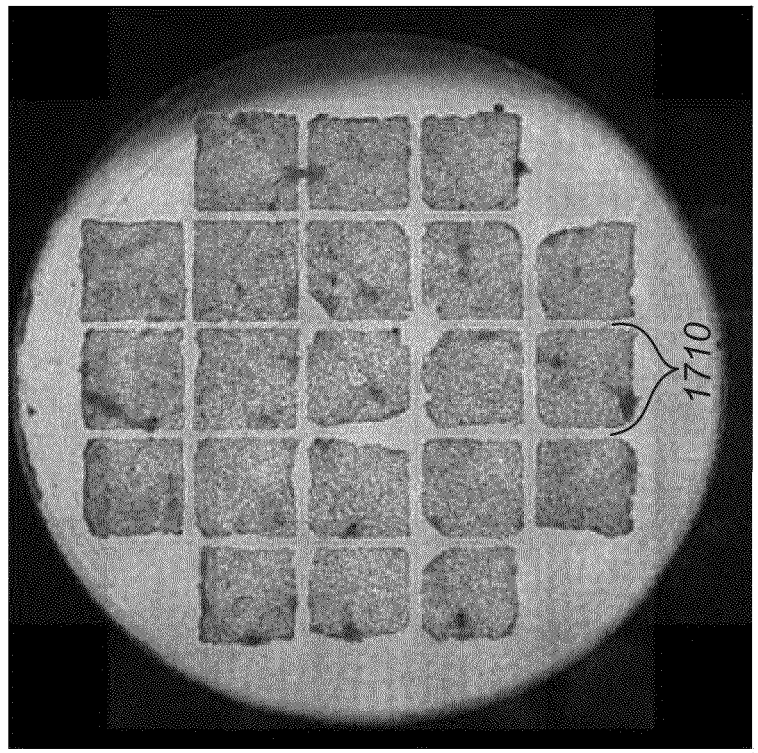
FIG. 17A diagrams the pattern of laser cutting lines positioned across the entire well used to section the iPS cell culture in FIG. 17B. The laser cutting lines 1710 are positioned to cut 1000 µm sections. Typical section sizes used to generate EBs from iPS and ES cells range from 250-2000 µm. The pulse spacing along the laser cutting lines 1710 is typically 16 µm, but may range from 5-50 µm. Dot 1720 indicates the position within the well where autofocusing and laser focusing will be performed. Areas 1730 define areas of the culture where the section size was less than the desired size (1000 µm) that were removed by the laser typically using 25 µm grid spacing, but can be performed using a range of laser grids from 5-100 µm. The image shows cultures sectioned into 1000 µm squares after removal of smaller sections.
Figure 17A:
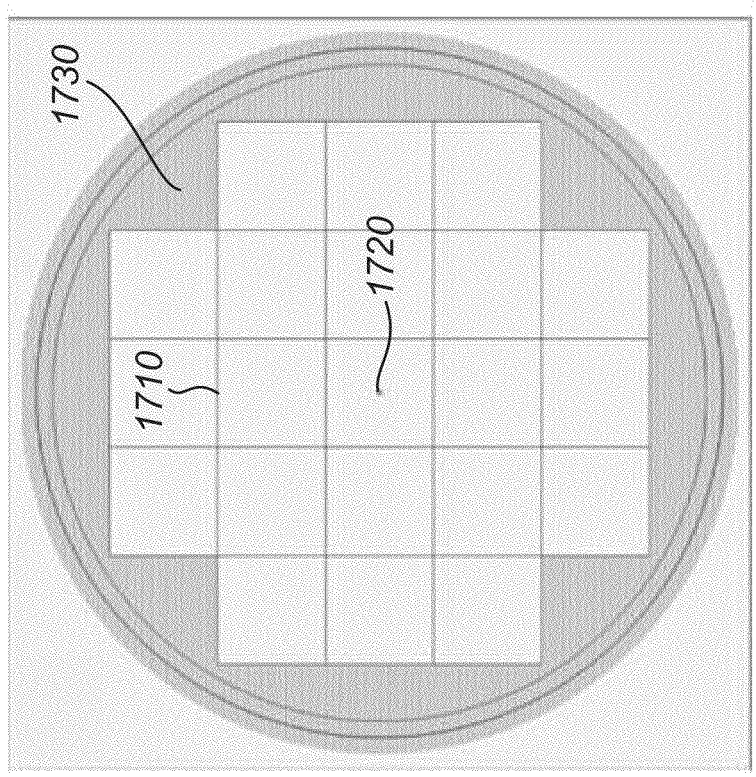
Figure 22B:
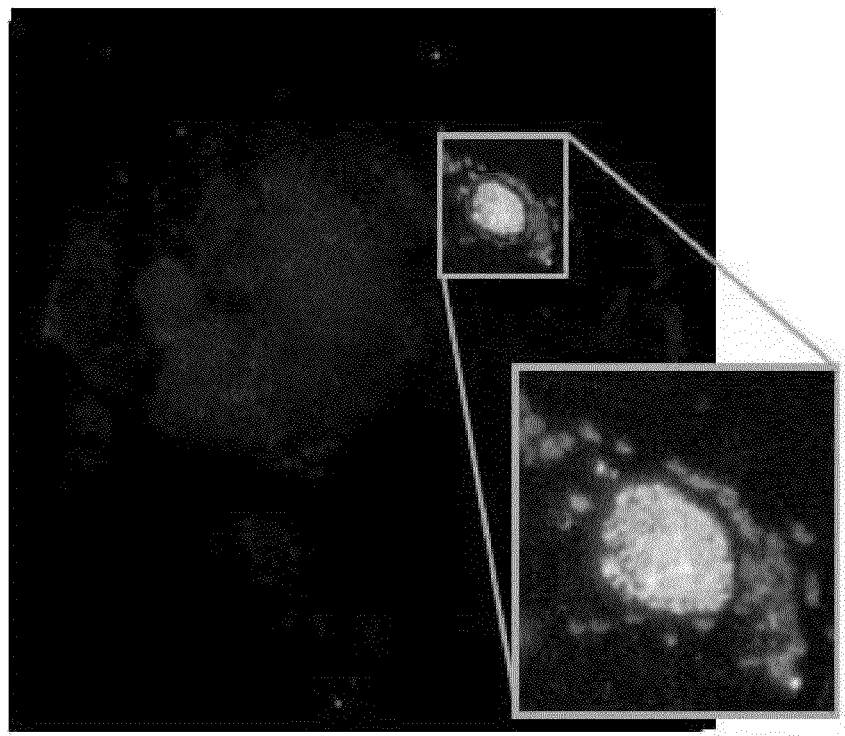
FIGS. 22A and 22B illustrate a brightfield image and a fluorescent image, respectively, of a human ES cell culture with variable expression of a nuclear marker (H2B tagged with green fluorescent protein). Image analysis was used to identify the ES cell colony with the highest expression of green fluorescent protein and to segment the edge of this colony. The images illustrate an ES cell colony with the edge the colony identified by image analysis prior to purification of the cell colony.
Figure 22A:
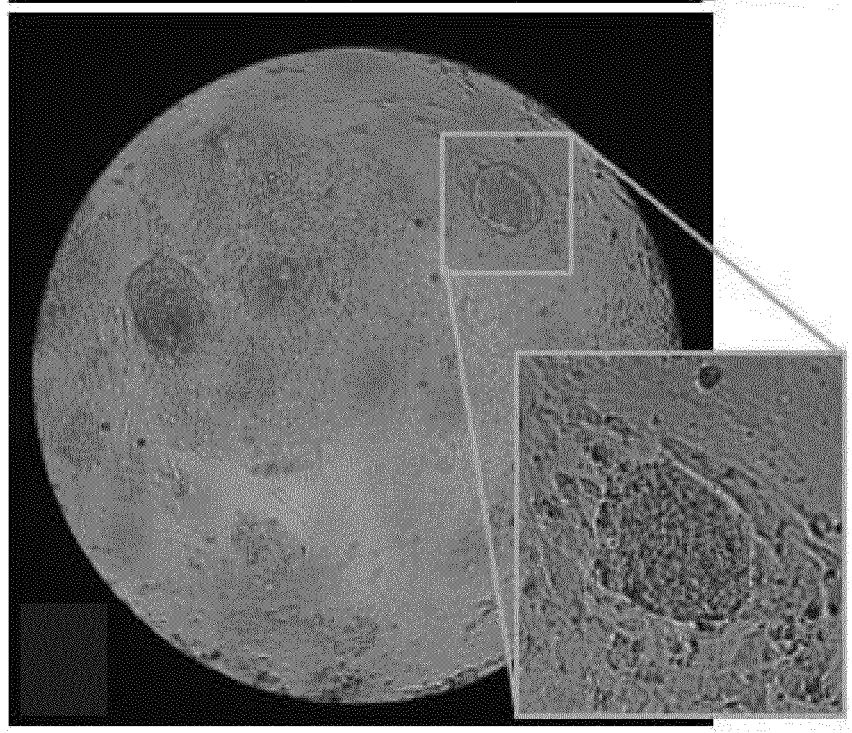
Figures 23A, 23B:
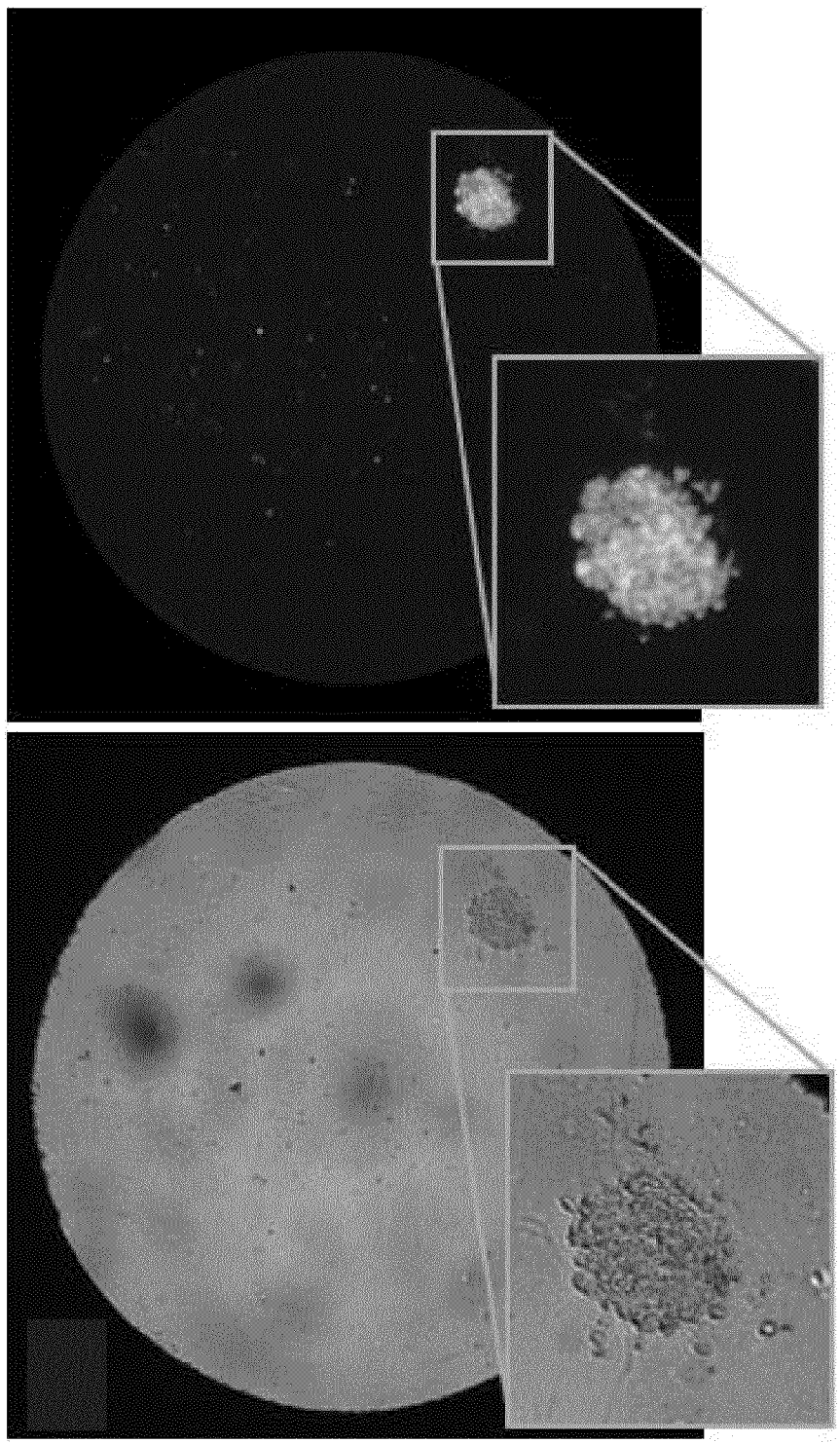
FIGS. 23A and 23B illustrate the purified ES cell colony of FIGS. 22A and 22B after a sequence of laser pulses were first delivered around the edge of the colony (separating the colony from the rest of the culture), followed by a grid pattern of laser pulses delivered to the rest of the culture (leaving only the ES colony remaining).

This experiment describes laser-mediated purification of human ES cell colonies for the purpose of generating genetically modified ES cell lines using the LEAP Workstation. Human ES cells, transduced one month earlier with a retrovirus containing a nuclear marker (H2B tagged with green fluorescent protein), were sectioned at high density by typical methodology (i.e., enzymatic treatment using collagenase IV (Invitrogen) onto 96-well plates (Corning)). Cultures were incubated in a cell culture incubator at 37° C. in complete stem cell medium for four days. On the fourth day, cultures were washed once with PBS (Invitrogen) and fresh stem cell medium containing 4 mg/ml Allura Red (Sigma) was added to the tissue culture wells for laser-mediated photothermal processing. Cultures were imaged using brightfield and fluorescence imaging on LEAP (FIG. 22) and human ES cell colonies were identified by morphology using brightfield images and by fluorescence intensity using fluorescent images. To produce a new cell line containing only cells expressing high levels of green fluorescent protein, the human ES cell colony with the highest fluorescence intensity within each well was segmented using LEAP stem cell manager software (FIG. 22). Once the colony to be isolated was selected, the edge of that colony was targeted using a series of 532 nm laser cutting lines at approximately 1 kHz, with an energy of 4.5 μJ per pulse and a laser spot radius of 6 μm delivered at the optimal laser focal plane as determined by a novel approach using LEAP. One repeat of one laser pulse was used to process a series of spots along the laser cutting line with a pulse spacing of 16 μm around the edge of each colony. Next, to purify only the selected colony, the remaining cells within the culture were eliminated using a series of 532 nm laser pulses in a grid across the culture at an energy of 4.5 μJ per pulse and a laser spot radius of 6 μm with a grid spacing of 25 μm. Two repeats of one laser pulse were used to eliminate all non-selected cells within the culture (FIG. 17, 23). Cultures can be processed using a range of laser energies from 1-50 μJ per pulse, laser spot size radii of 1-20 μm, pulse spacing of 5-50 μm, grid spacing of 5-100 μm, using 1-5 repeats per spot. Isolation of the selected colony allows only the cells within this colony to grow and thus generate the new cell line. Cultures were washed and fresh stem cell medium containing fresh inactivated murine embryonic fibroblasts was added to the tissue culture wells. Addition of a fresh matrix (murine embryonic fibroblasts) allowed the colony to expand until reaching a large enough size for propagation, at which time the new cell line had been derived. New human ES cell lines generated by this method were monitored for several months and retained a morphology characteristic of ES cells and continued to express high levels of green fluorescent protein. Human ES cell lines generated by the colony purification method expressed green fluorescent protein more homogeneously than typical methods of stem cell line generation (i.e., enzymatic passage of stem cell cultures in the presence of antibiotic selection, shown in FIG. 22). New stem cell lines can be produced more efficiently using this automated method of high throughput colony isolation rather than typical colony isolation methods which involve manual physical circumscribing of each colony with a needle within a culture plate with fairly large wells.

This example describes the isolation and purification of human ES cell colonies allowing increased efficiency of production of new stem cell lines. The method used to isolate stem cell colonies is highly reproducible and automated, making it very useful for generating genetically modified stem cell lines and for the production of newly derived ES and iPS cell lines.

The following publications are related to the technology described herein and are incorporated herein by reference in their entireties for all of their methods, compositions, devices, etc., all of which can be utilized with the methods, systems and apparatus described herein, in any combination:

Thomson J. A, et al. "Embryonic stem cell lines derived from human blastocysts" (1998) Science; 282:1145-1147; Reubinoff B. E., et al. "Embryonic stem cell lines from human blastocyst: Somatic differentiation in vitro. (2000) Nat. Biotechnol; 18:399-404"; Draper J. S., et al. "Recurrent gains of chromosomes 17q and 12 in cultured human embryonic stem cells" (2004) Nat. Biotechnol.; 22:53-54; Buzzard J. J., et al. "Karyotype of human ES cells during extended culture" (2004) Nat. Biotechnol.; 22:381-382; Mitalipova M., et al. "Preserving the genetic integrity of human embryonic stem cells" (2005) Nat. Biotechnol.; 23:19-20"; Oh S. K., et al. "Methods for expansion of human embryonic stem cells" (2005) Stem Cells; 23:605-609; Joannides A., et al. "Automated Mechanical Passage: A novel and efficient method for human embryonic stem cell expansion" (2006) Stem Cells 24:230-235; Thomson, H., "Bioprocessing of embryonic stem cells for drug discovery" Review. (2007) Trends Biotechnol.; 25:224-230; Terstegge S., et al. "*Automated maintenance of embryonic stem cell cultures*" (2007) Biotechnol. Bioeng.; 96:195-201; Takahashi K., et al. "Induction of pluripotent stem cells from adult human fibroblast by defined factors" (2007) Cell; 131: 861-872; Koller, M R., "High-Throughput Laser-Mediated In Situ Cell Purification With High Purity and Yield" (2004) Cytometry; 61A: 153-161; Valamehr B., et al. "Hydrophobic surfaces for enhanced differentiation of embryonic stem cell-derived embryoid bodies" (2008) PNAS; 105:14459-14464; Bauwens C., et al. "Control of human embryonic stem cell colony and aggregate size heterogeneity influences differentiation trajectories" (2008) Stem Cells; 26:2300-2310; Ungrin M., et al. "Reproducible, ultra high-throughput formation of multicellular organization from single cell suspension-derived human embryonic stem cell aggregates" (2008) PLOS One; 3:1565-1-12; Burridge P., et al. "Improved human embryonic stem cell embryoid body homogeneity and cardiomyocyte differentiation from a novel V-96 plate aggregation system highlights interline variability (2007) Stem Cells; 25:929-938. Other publications related to the present technology include U.S. Pat. Nos. 7,129,070; 6,534,308 and 6,514,722. Each of the above-listed publications is hereby incorporated by reference in its entirety.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of sectioning a stem cell colony, comprising:
providing a cell culture comprising at least one living stem cell colony on a culture surface;
imaging the surface;
selecting a stem cell colony for sectioning that exhibits an undifferentiated phenotype for the stem cell colony, which phenotype is shown in the image;
identifying at least a portion of the edge of the stem cell colony in the image;
applying electromagnetic radiation to the identified edge of the stem cell colony to separate the colony from rest of the culture; and defining a grid pattern of cutting lines which grid pattern defines a plurality of sub colonies of generally uniform size from the selected stem cell colony; and applying electromagnetic energy in the grid pattern of the cutting lines at the culture surface so as to section the living stem cell colony into the plurality of sub colonies of generally uniform size, wherein the applying electromagnetic radiation in the grid pattern comprises one or more of: the use of a series of laser pulses which may be emitted using a range of laser energies from about 1 to about 50 µJ per pulse; the use of a series of laser pulses which may be emitted using a range of laser spot radii from about 1 to about 20 µm; and the use of a series of 532 nm laser pulses which may be emitted using 1 to 5 laser pulses.

2. The method of sectioning a stem cell colony of claim 1 further comprising adding a dye configured to increase absorbance of the laser energy.

3. The method of sectioning a stem cell colony of claim 1, wherein the pattern of electromagnetic cutting lines is limited to within the boundaries of the cell colony.

4. The method of sectioning a stem cell colony of claim 1, further comprising segmenting the imaged cell colony prior to sectioning the colony.

5. The method of sectioning a stem cell colony of claim 1, wherein applying electromagnetic radiation in the grid pattern comprises the use of a series of laser pulses which may be emitted using a range of laser energies from about 1 to about 50 µJ per pulse.

6. The method of sectioning a stem cell colony of claim 1, wherein applying electromagnetic radiation in the grid pattern comprises use of a series of laser pulses which may be emitted using a range of laser spot radii from about 1 to about 20 µm.

7. The method of sectioning a stem cell colony of claim 1, wherein applying electromagnetic radiation in the grid pattern comprises use of a series of 532 nm laser pulses which may be emitted using 1 to 5 laser pulses.

8. The method of sectioning a stem cell colony of claim 1, wherein applying electromagnetic radiation in the grid pattern comprises use of a series of approximately 532 nm laser pulses which may be emitted using between 1 and 5 laser repeats.

9. The method of sectioning a stem cell colony of claim 1, wherein applying electromagnetic radiation in the grid pattern comprises a pattern of laser cutting lines with pulse spacing between about 5 to about 50 µm.

10. The method of sectioning a stem cell colony of claim 1, wherein applying electromagnetic radiation in the grid pattern comprises a pattern of laser grids with grid spacing between about 5 to about 100 µm.

11. The method of sectioning a stem cell colony of claim 1, wherein applying electromagnetic radiation in the grid pattern comprises a square pattern of laser cutting lines positioned about 20 to about 2000 µm.

12. The method of sectioning a stem cell colony of claim 1, wherein applying electromagnetic radiation in the grid pattern comprises a square pattern of laser cutting lines positioned about 20 to about 300 µm apart for enzyme-free removal of sections.

13. The method of sectioning a stem cell colony of claim 1, wherein applying electromagnetic radiation in the grid pattern comprises a square pattern of laser cutting lines positioned about 250 to about 2000 µm apart for use in differentiation of stem cells into mature specialized cell types.

14. The method of sectioning a stem cell colony of claim 1 further comprising adding a dye configured to increase absorbance of the electromagnetic radiation.

15. The method of sectioning a stem cell colony of claim 1 further comprising applying electromagnetic radiation to an edge of the cell colony to isolate the living stem cell colony from rest of the culture.

16. The method of sectioning a stem cell colony of claim 1 further comprising removing one or more of the sectioned sub colonies.

17. The method of sectioning a stem cell colony of claim 16, wherein removing one or more of the sectioned sub colonies comprises dislodging the one or more sectioned sub colonies into suspension within the fluid of a first culture vessel.

18. The method of sectioning a stem cell colony of claim 16, wherein removing the sectioned one or more sectioned sub colonies comprises addition of chemicals, such as enzymes, prior to dislodging the one or more sectioned sub colonies into suspension within the fluid of the first culture vessel.

19. The method of sectioning a stem cell colony of claim 16 further comprising transferring the one or more sectioned sub colonies to a second culture vessel.

20. The method of sectioning a stem cell colony of claim 16, wherein removing the sectioned one or more sectioned sub colonies comprises a fluid pipetting technique.

21. The method of sectioning a stem cell colony of claim 16 further comprising washing out remaining feeder layer.

22. The method of sectioning a stem cell colony of claim 1, wherein the cell colony comprises living embryonic or induced pluripotent stem cells.

23. The method of sectioning a stem cell colony of claim 1, wherein the cell colony comprises embryonic stem cells or induced pluripotent stem cells.

* * * * *